United States Patent
Asada

(10) Patent No.: US 11,262,602 B2
(45) Date of Patent: Mar. 1, 2022

(54) HOLDING TOOL FOR WEARABLE DEVICE AND FACE OR HEAD-MOUNTED IMPLEMENT PROVIDED WITH HOLDING TOOL

(71) Applicant: YAMAMOTO KOGAKU CO., LTD., Higashiosaka (JP)

(72) Inventor: Masataka Asada, Higashiosaka (JP)

(73) Assignee: YAMAMOTO KOGAKU CO., LTD., Higashiosaka (JP)

(*) Notice: Subject to any disclaimer, the term of this patent is extended or adjusted under 35 U.S.C. 154(b) by 347 days.

(21) Appl. No.: 16/608,053

(22) PCT Filed: Apr. 12, 2018

(86) PCT No.: PCT/JP2018/015313
§ 371 (c)(1),
(2) Date: Oct. 24, 2019

(87) PCT Pub. No.: WO2018/198780
PCT Pub. Date: Nov. 1, 2018

(65) Prior Publication Data
US 2020/0201081 A1    Jun. 25, 2020

(30) Foreign Application Priority Data
Apr. 28, 2017   (JP) .............................. JP2017-089235

(51) Int. Cl.
*G02C 1/00* (2006.01)
*G02C 11/00* (2006.01)
(Continued)

(52) U.S. Cl.
CPC .............. *G02C 11/10* (2013.01); *A42B 3/185* (2013.01); *G02B 27/0176* (2013.01);
(Continued)

(58) Field of Classification Search
CPC . G02C 11/10; G02C 1/10; G02C 1/00; G02C 7/086; G02C 9/00; G02B 27/0176; G02F 1/163
(Continued)

(56) References Cited

U.S. PATENT DOCUMENTS

2008/0169998 A1    7/2008  Jacobsen et al.
2010/0245756 A1*   9/2010  Sugihara ............ G02B 27/0172
                                                    351/158

FOREIGN PATENT DOCUMENTS

CN    205539727 U    4/2016
JP         072088    5/1984
(Continued)

OTHER PUBLICATIONS

International Search Report issued in PCT/JP2018/015313 dated Jun. 26, 2018.
(Continued)

*Primary Examiner* — Hung X Dang
(74) *Attorney, Agent, or Firm* — Heslin Rothenberg Farley and Mesiti PC; Nicholas Mesiti

(57) ABSTRACT

A holding tool is capable of performing positioning and reliable attachment by simple insertion operation when attaching a wearable device, and is capable of performing reliable detachment by simple operation when the device is detached. When a body part of a wearable device is inserted into a holding frame body, a projected engagement part of an elastic pressing body provided in the holding frame body is engaged with an upper surface and/or a lower surface of the body part. Engagement between the upper surface and/or the lower surface of the body part and the projected engagement part of the elastic pressing body is released by operating an (Continued)

operation part of the elastic pressing body upward and/or downward, to allow the wearable device to be pulled out of the holding frame body.

19 Claims, 39 Drawing Sheets

(51) Int. Cl.
    *A42B 3/18*     (2006.01)
    *G06F 1/16*     (2006.01)
    *G02C 9/00*     (2006.01)
    *G02C 7/08*     (2006.01)
    *G02B 27/01*     (2006.01)

(52) U.S. Cl.
    CPC ............... *G02C 7/086* (2013.01); *G02C 9/00* (2013.01); *G06F 1/163* (2013.01)

(58) Field of Classification Search
    USPC .................................................... 351/158, 41
    See application file for complete search history.

(56) References Cited

FOREIGN PATENT DOCUMENTS

| | | |
|---|---|---|
| JP | 11984072088 U | 5/1984 |
| JP | 2007178939 A | 7/2007 |
| JP | 2010516186 A | 5/2010 |
| JP | 2016076447 A | 5/2016 |

OTHER PUBLICATIONS

International Preliminary Report on Patentability issued in PCT/JP2018/015313 dated Oct. 29, 2019.

* cited by examiner

US 11,262,602 B2

HOLDING TOOL FOR WEARABLE DEVICE AND FACE OR HEAD-MOUNTED IMPLEMENT PROVIDED WITH HOLDING TOOL

CROSS REFERENCE TO RELATED APPLICATIONS

This application is the National Phase filing under 35 U.S.C. § 371 of International Application No.: PCT/JP2018/015313, filed on Apr. 12, 2018, and published on Nov. 1, 2018 as WO 2018/198780 A1, which claims priority to Japanese Application No.: 2017-089235, filed on Apr. 28, 2017. The contents of each of these prior applications are hereby incorporated by reference herein in their entirety.

TECHNICAL FIELD

The present invention relates to a holding tool for a wearable device such as a head-mounted display, and a face or head-mounted implement such as glasses, goggles, a helmet and a head band provided with this holding tool.

BACKGROUND ART

Conventionally, glasses including openings that are provided in temple parts, and engage with a wearable device, and regulating parts that regulate dropping of the wearable device from the temple parts exist as a face or head-mounted implement provided with this kind of holding tool. In these glasses, the wearable device can be detached from the temple parts by turning operation of the regulating parts. (Patent Literature 1: Japanese Patent Laid-Open No. 2016-224232)

The glasses thus configured enable various wearable devices to be detached, and these wearable devices are not dropped by movement of a user, and an attached wearable device can be simply replaced with other wearable device. Additionally, a user can replace the wearable devices even in a state of wearing the glasses at the time of replacement.

SUMMARY OF INVENTION

Technical Problem

However, in the glasses disclosed in Patent Literature 1, in order to fix the position of the wearable device after the wearable device is engaged with the openings provided in the temple parts, a lock mechanism separately needs to be operated after the device is fixed at a fixed position, and there is a problem that the wearable device cannot be easily attached or detached, and handling is troublesome.

In the aforementioned glasses, the wearable device is displaced on the outside of lens parts of the glasses, and therefore there is a problem that in use outdoors at the time of rainfall or snowfall, use under bad environment such as inside of a factory where flying objects are flying, or dust is falling, a display part that projects an image or the like of the device gets wet, is stained, or is damaged, the image or the like on the display part is difficult to be seen, and furthermore failure is caused.

The present invention has been made in order to solve the aforementioned conventional problems, and an object of the present invention is to provide a holding tool for a wearable device, and a face or head-mounted implement provided with this holding tool, in which when a wearable device is attached, the wearable device can be positioned and reliably attached by simple insertion operation without separately operating a lock mechanism, and when the device is detached, the device can be reliably detached by simple operation, and a display part of the wearable device is unlikely to get wet, be stained, or be damaged.

Solution to Problem

Therefore, in a holding tool for a wearable device of the present invention, a body part 22 of a wearable device 21 is detachably attached to a holding frame body 11, a projected engagement part 12 of an elastic pressing body 13 provided in at least one of an upper frame part 11a and a lower frame part 11b of the holding frame body 11 is detachably engaged with at least one of an upper surface 22a and a lower surface 22b of the body part 22 of the wearable device 21, when the body part 22 of the wearable device 21 is inserted into the holding frame body 11, the projected engagement part 12 of the elastic pressing body 13 is engaged with the upper surface 22a and/or the lower surface 22b of the body part 22, engagement between the upper surface 22a and/or the lower surface 22b of the body part 22 and the projected engagement part 12 of the elastic pressing body 13 is released by operating an operation part 13a of the elastic pressing body 13 upward and/or downward, and the wearable device 21 is pulled out of the holding frame body 11.

Furthermore, in a holding tool for a wearable device of the present invention, a body part 22 of a wearable device 21 is detachably attached to a holding frame body 11, a projected engagement part 12 of an elastic pressing body 13 provided in at least one of an upper surface 22a and a lower surface 22b of the body part 22 is detachably engaged with at least one of an upper frame part 11a and a lower frame part 11b of the holding frame body 11, when the body part 22 of the wearable device 21 is inserted into the holding frame body 11, the projected engagement part 12 of the elastic pressing body 13 is engaged with the upper frame part 11a and/or the lower frame part 11b of the holding frame body 11, engagement between the upper frame part 11a and/or the lower frame part 11b of the holding frame body 11 and the projected engagement part 12 of the elastic pressing body 13 is released by operating an operation part 13a of the elastic pressing body 13 downward and/or upward, and the wearable device 21 is pulled out of the holding frame body 11.

In the holding tool for a wearable device of the present invention, a recessed engagement part 23 is formed in at least one of the upper surface 22a and the lower surface 22b of the body part 22 of the wearable device 21, the projected engagement part 12 of the elastic pressing body 13 is operated upward and/or downward by an end of the upper surface 22a and/or the lower surface 22b of the body part 22, and the projected engagement part 12 of the elastic pressing body 13 is engaged with the recessed engagement part 23 of the body part 22 so as to slide in the recessed engagement part 23.

In the holding tool for a wearable device of the present invention, a projected engagement part 14 is formed in at least one of the upper frame part 11a and the lower frame part 11b of the holding frame body 11, and the projected engagement part 12 of the elastic pressing body 13 slides over the projected engagement part 14 of the holding frame body 11 to be engaged with the projected engagement part 14.

In the holding tool for a wearable device of the present invention, the holding frame body 11 is a rectangular frame body including the upper frame part 11a, the lower frame part 11b, a front frame part 11c, and a rear frame part 11d.

In the holding tool for a wearable device of the present invention, in a state in which a part of the upper surface 22a of the body part 22 of the wearable device 21 is in contact with an inner surface of the upper frame part 11a of the holding frame body 11, or a part of the lower surface 22b of the body part 22 of the wearable device 21 is in contact with an inner surface of the lower frame part 11b of the holding frame body 11, the body part 22 of the wearable device 21 is inserted into the holding frame body 11.

In the holding tool for a wearable device of the present invention, a recessed wall 26 is formed on a front surface 22c of the body part 22 of the wearable device 21, a projected wall 27 is formed on a rear surface 22d of the body part 22, the recessed wall 26 is in contact with an inner surface of the front frame part 11c of the holding frame body 11, and the projected wall 27 is in contact with an inner end of the rear frame part 11d of the holding frame body 11.

In the holding tool for a wearable device of the present invention, the projected engagement part 12 of the elastic pressing body 13 is a part obtained by protruding an intermediate part of the elastic pressing body 13 in a width direction so as to have a substantially V-shape, and the recessed engagement part 23 of the body part 22 of the wearable device 21 is a groove formed in a substantially V-shape in a width direction of at least one of the upper surface 22a and the lower surface 22b of the body part 22.

In the holding tool for a wearable device of the present invention, the projected engagement part 12 of the elastic pressing body 13 is a part obtained by protruding an intermediate part of the elastic pressing body 13 in a width direction so as to have a substantially V-shape, and the projected engagement part 14 of the holding frame body 11 is a projection formed in a substantially V-shape in a width direction of at least one of inner surfaces of the upper frame part 11a and the lower frame part 11b of the holding frame body 11.

A face or head-mounted implement of the present invention includes the holding frame body 11 of the holding tool provided in one side end of a lens body part 1, wherein a display part 24 of the wearable device 21 is glasses disposed on an inner side of a lens 3.

A face or head-mounted implement of the present invention includes the holding frame body 11 of the holding tool provided in one side end of a lens body part 1, wherein a display part 24 of the wearable device 21 is glasses disposed on an outer side of a lens 3.

A face or head-mounted implement of the present invention includes the holding frame body 11 of the holding tool provided in one side end of a clamping body 8 formed in an inverted substantially U-shape and having elasticity, wherein a display part 24 of the wearable device 21 is a head band disposed in a region where a wearer is capable of seeing the display part 24.

A face or head-mounted implement of the present invention includes the holding frame body 11 of the holding tool provided on an inner or outer side of a cheek side part 9a on one side of a shell 9, wherein a display part 24 of the wearable device 21 is a helmet disposed in a region where a wearer is capable of seeing the display part 24.

Advantageous Effect of Invention

The present invention is configured as described above, and therefore when a wearable device is attached, positioning and reliable attachment can be performed by simple insertion operation, and when the device is detached, reliable detachment can be performed by simple operation, and therefore it is very easy to handle.

Furthermore, in the present invention, a display part that projects an image or the like of the wearable device is disposed on an inner side of a lens body part, so that the display part is unlikely to get wet, be stained, or be damaged, and therefore the image or the like on the display part is not difficult to be seen, and furthermore failure is unlikely to occur, and longtime use in a preferable state is possible.

DESCRIPTION OF EMBODIMENTS

Figure 1:
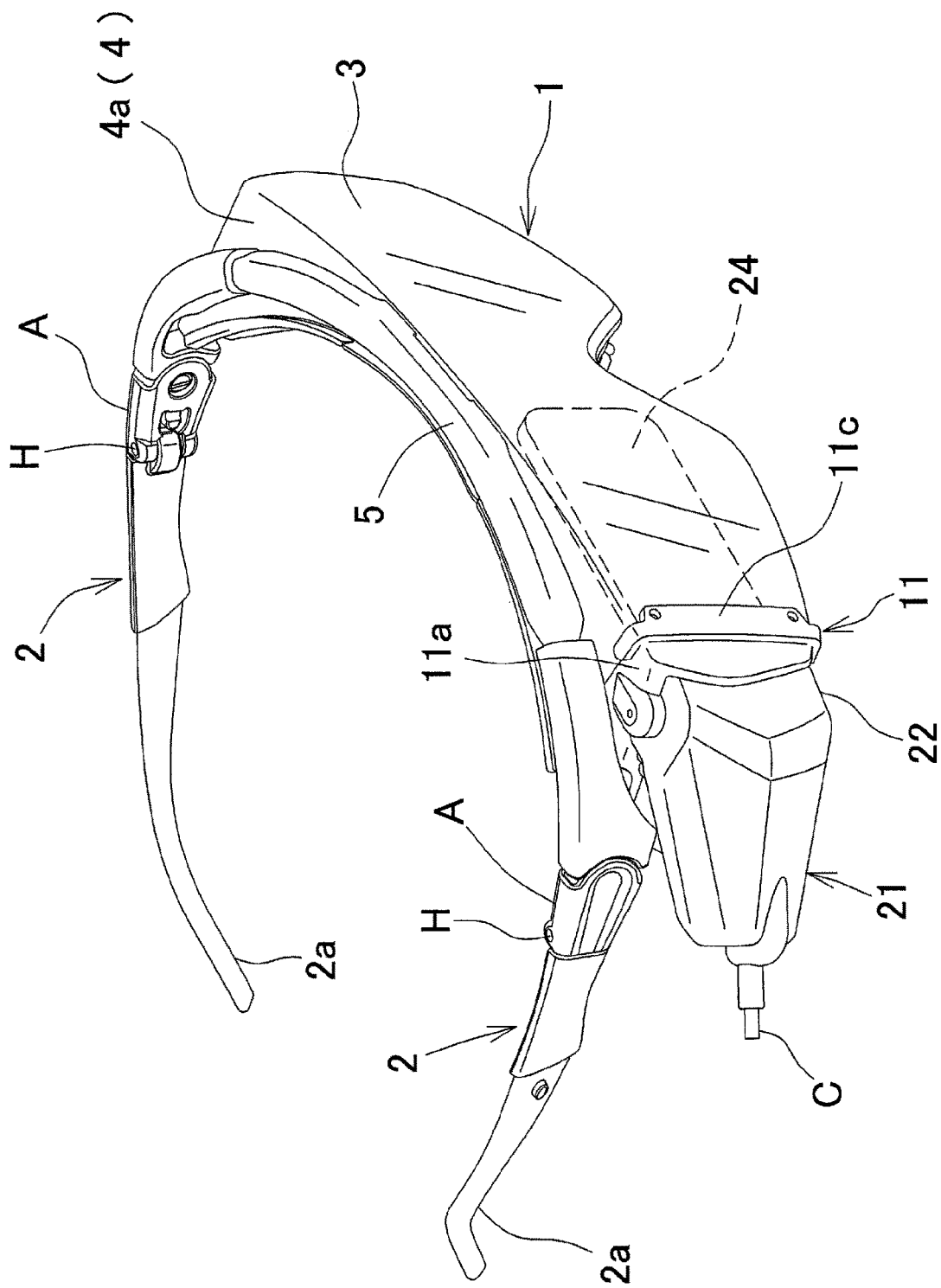
FIG. 1 is a perspective view illustrating a first embodiment in which a holding tool of the present invention is provided in a face or head-mounted implement which is glasses.
Figure 2:
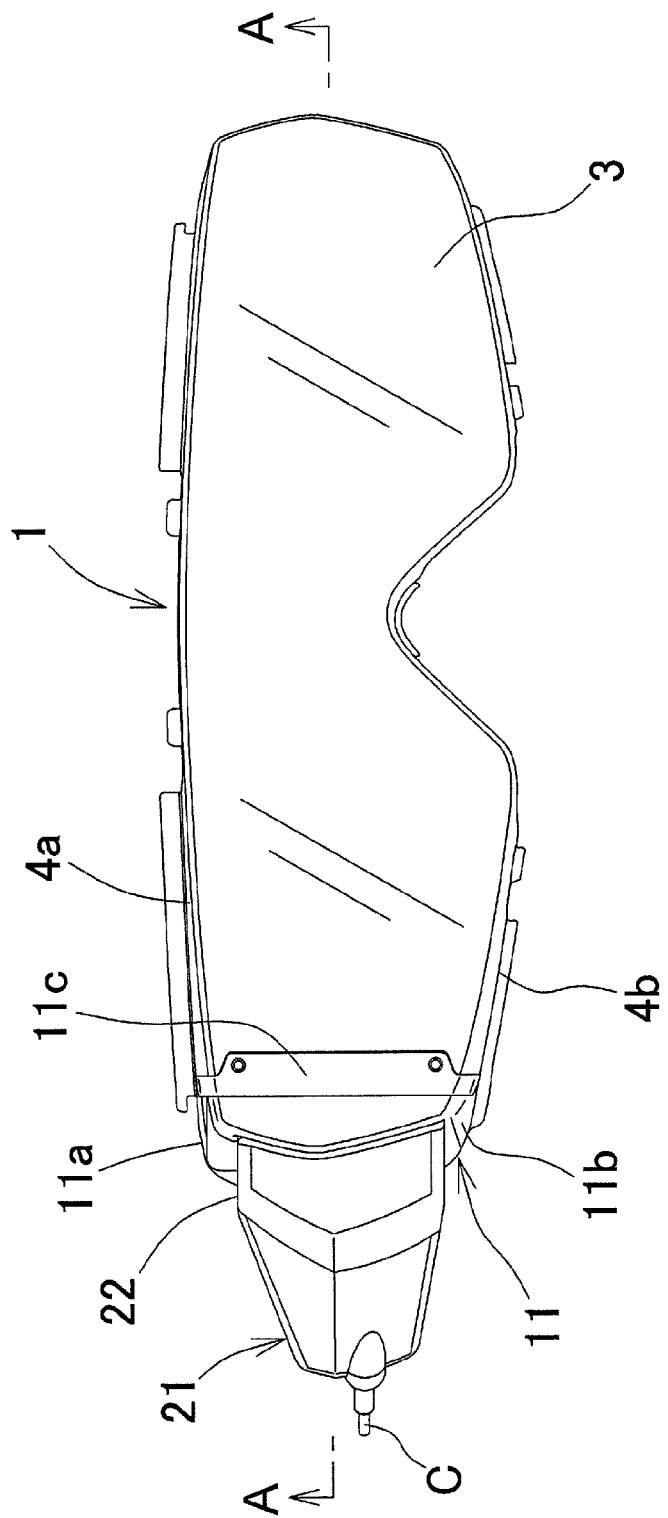
FIG. 2 is a front view of a main part of the face or head-mounted implement illustrated in FIG. 1.
Figure 3:
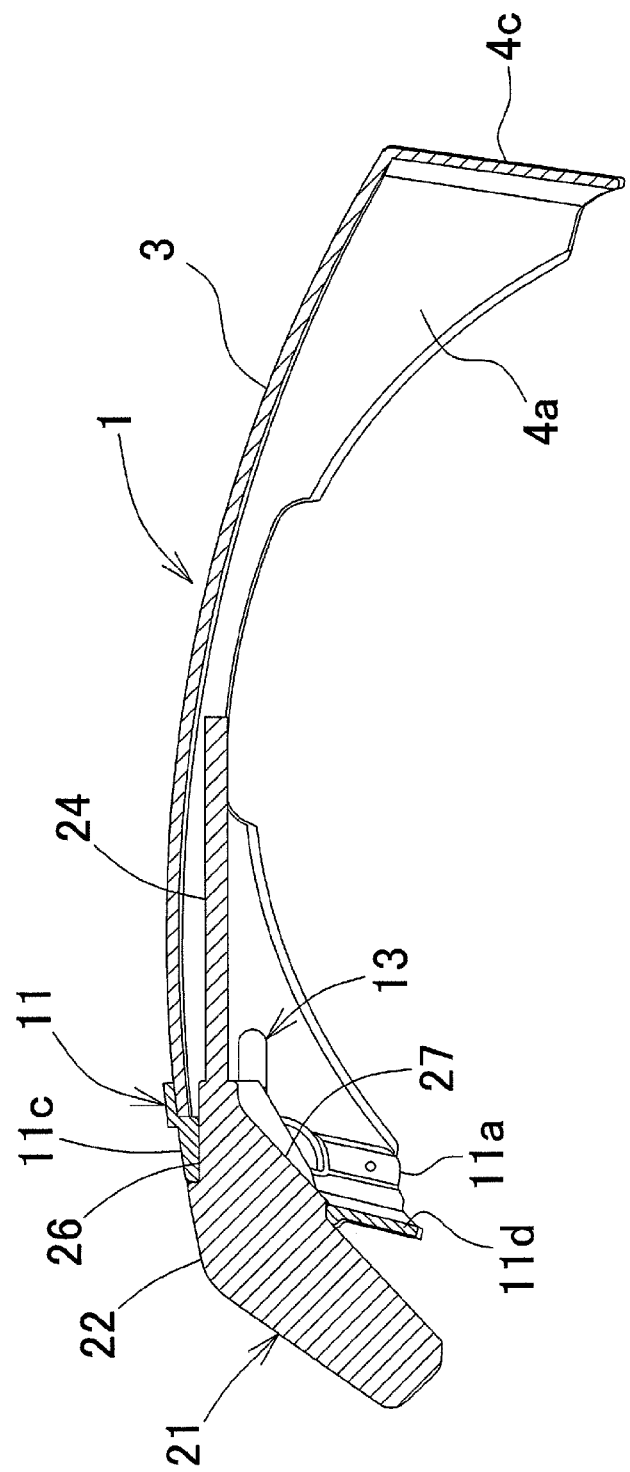
FIG. 3 is a sectional view taken along the line A-A in FIG. 2.
Figure 4:
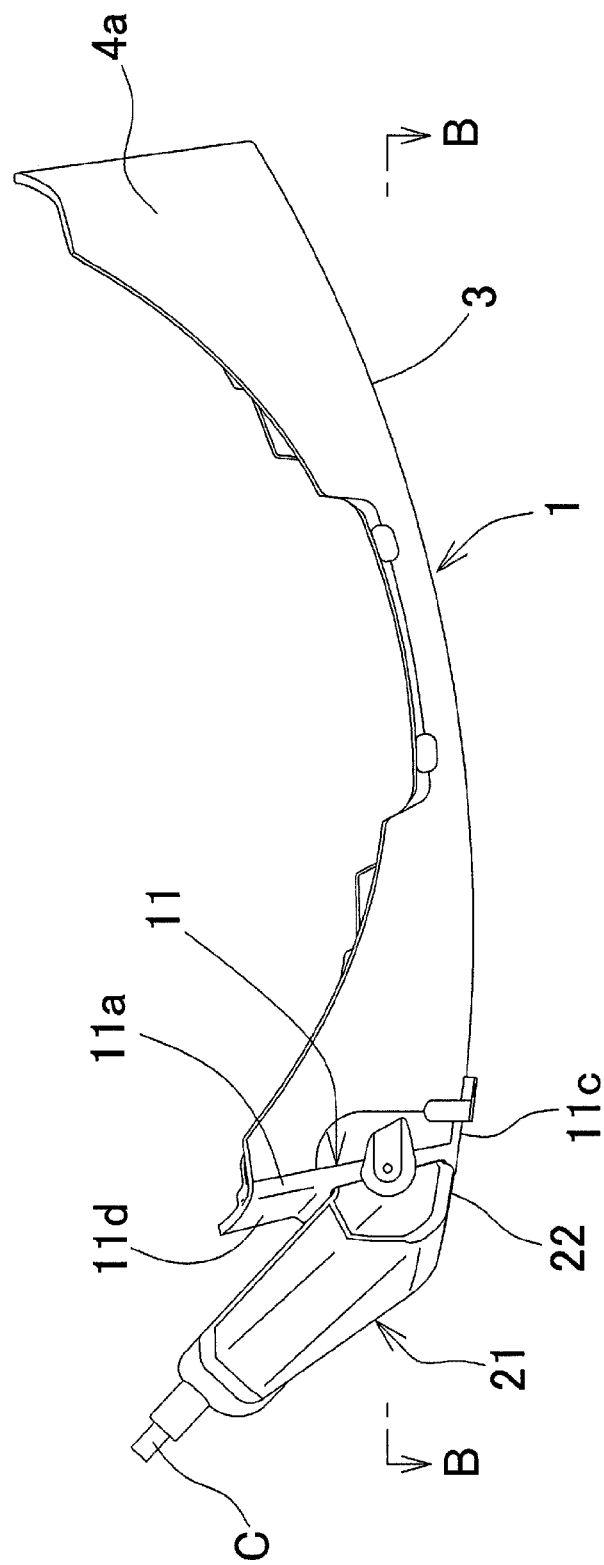
FIG. 4 is a plan view of the main part of the face or head-mounted implement illustrated in FIG. 1.
Figure 5:
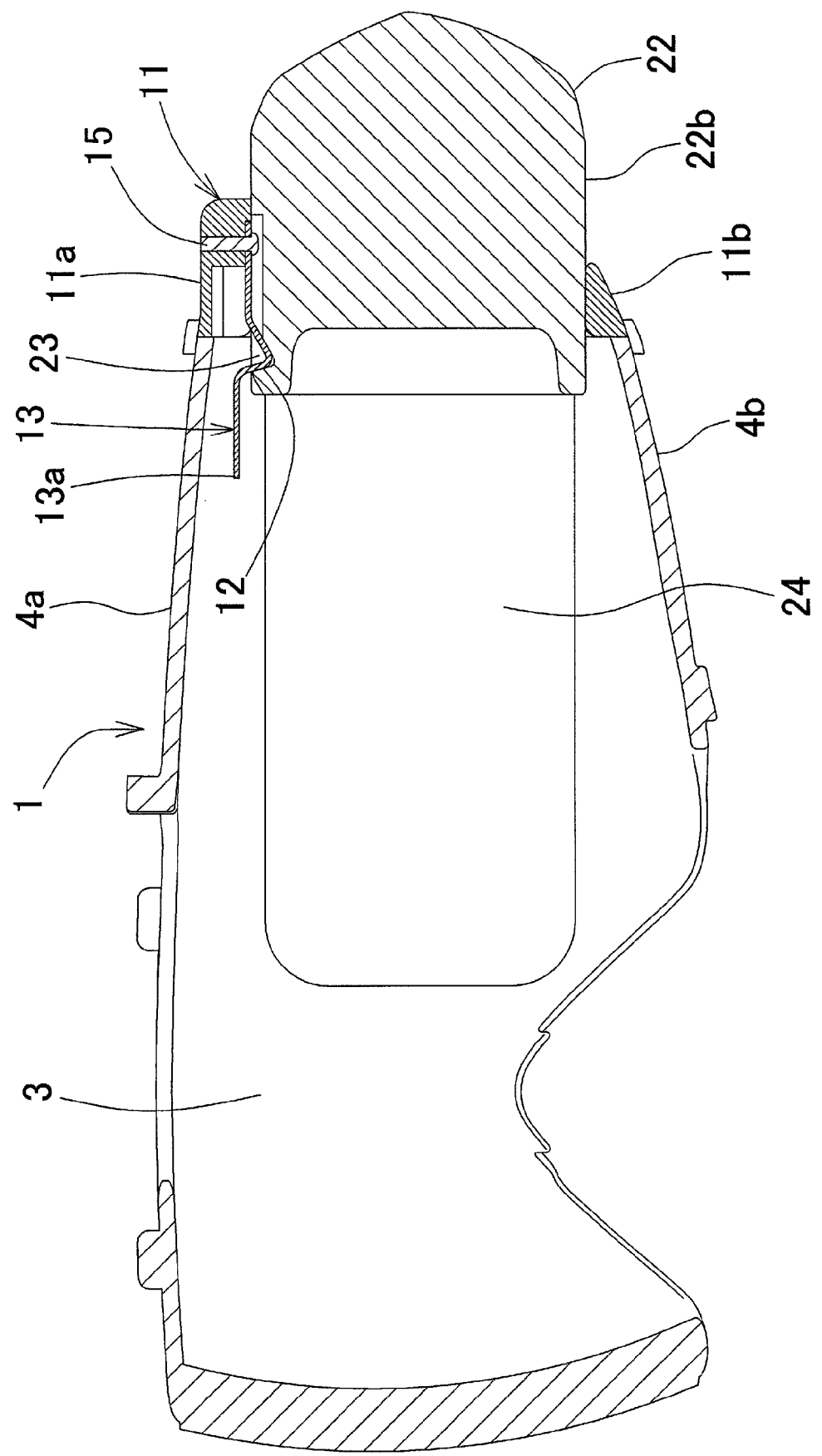
FIG. 5 is a sectional view taken along the line B-B in FIG. 4.
Figure 6:
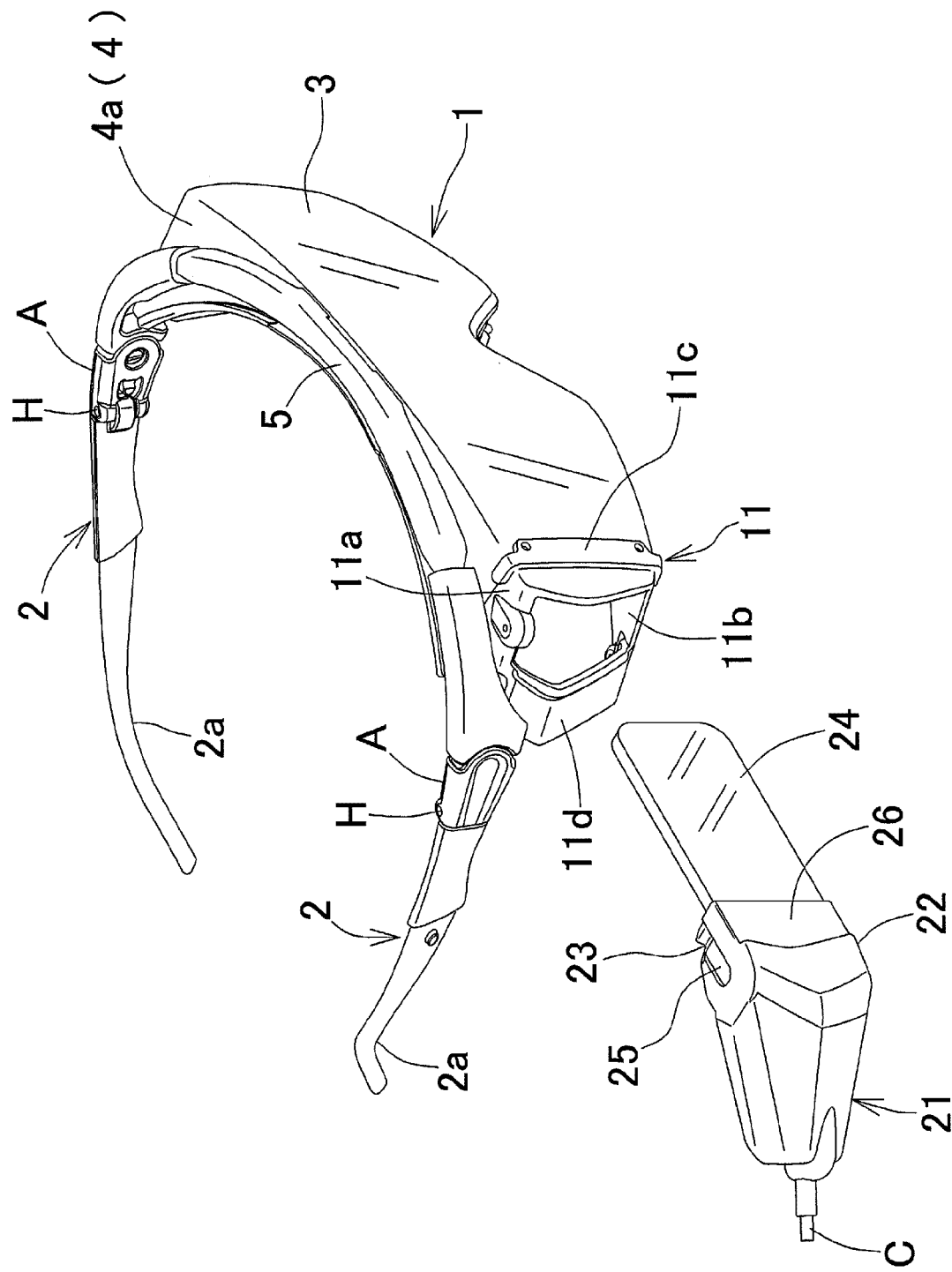
FIG. 6 is a perspective view in a state in which a wearable device is detached from the face or head-mounted implement illustrated in FIG. 1.
Figure 7:
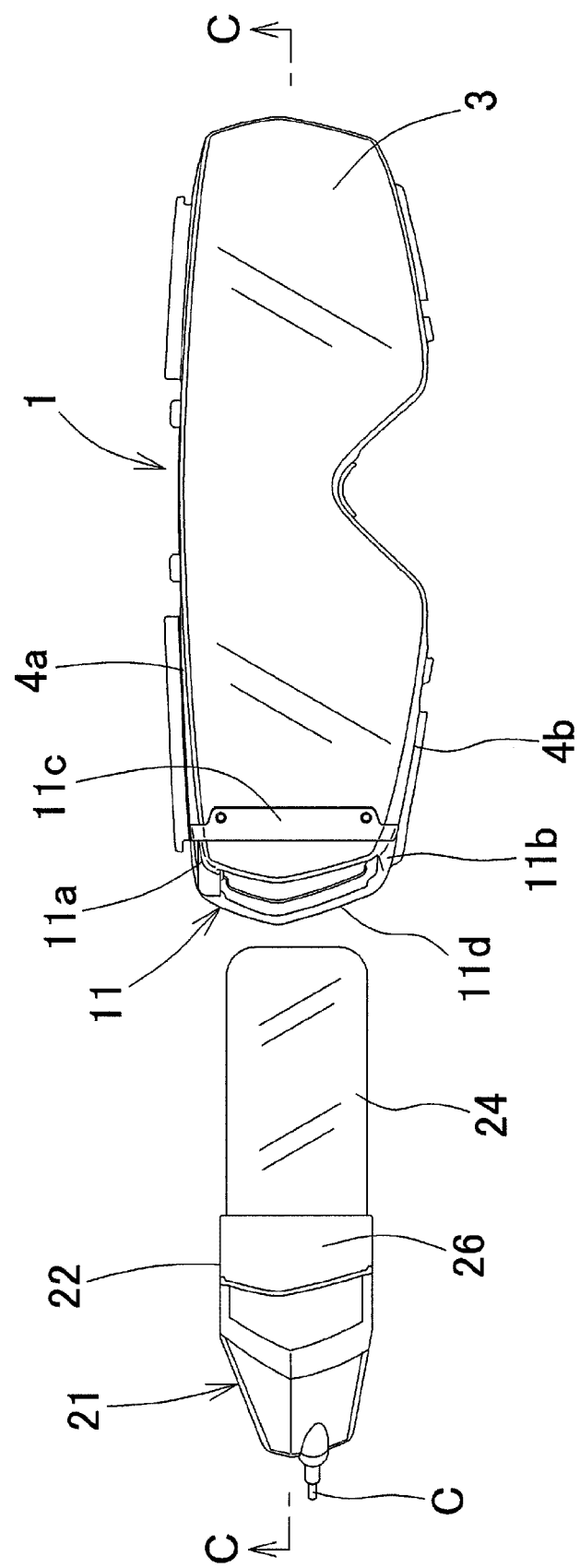
FIG. 7 is a front view of the main part of the face or head-mounted implement in a state illustrated in FIG. 6.
Figure 8:
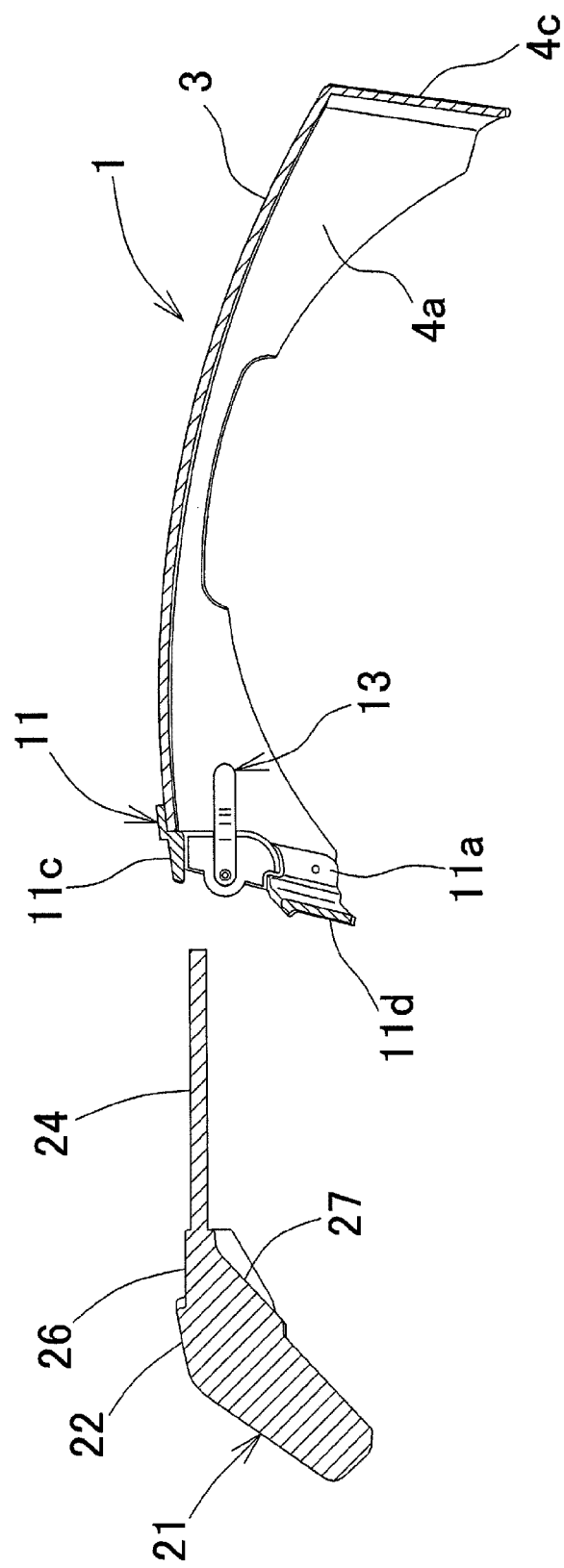
FIG. 8 is a sectional view taken along the line C-C in FIG. 7.
Figure 9:
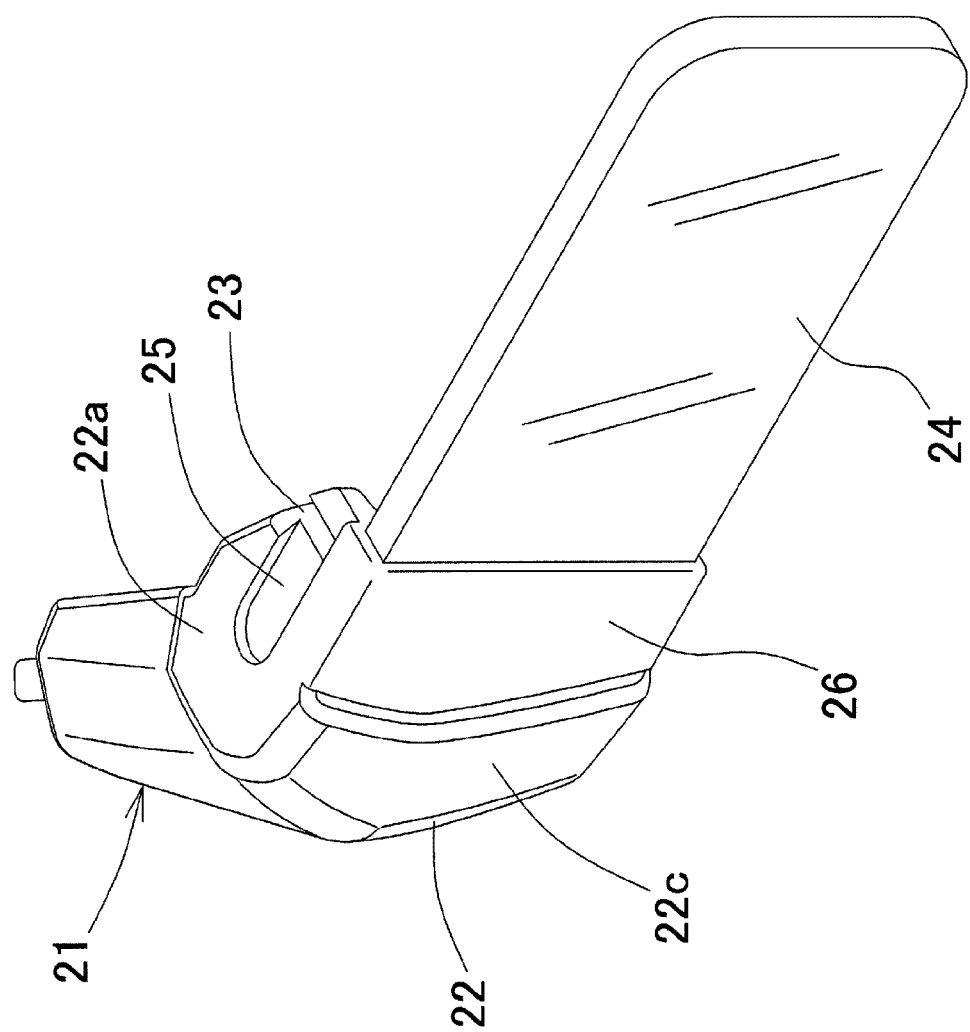
FIG. 9 is a perspective view of the wearable device detachably attached to the holding tool of the present invention.
Figure 10:
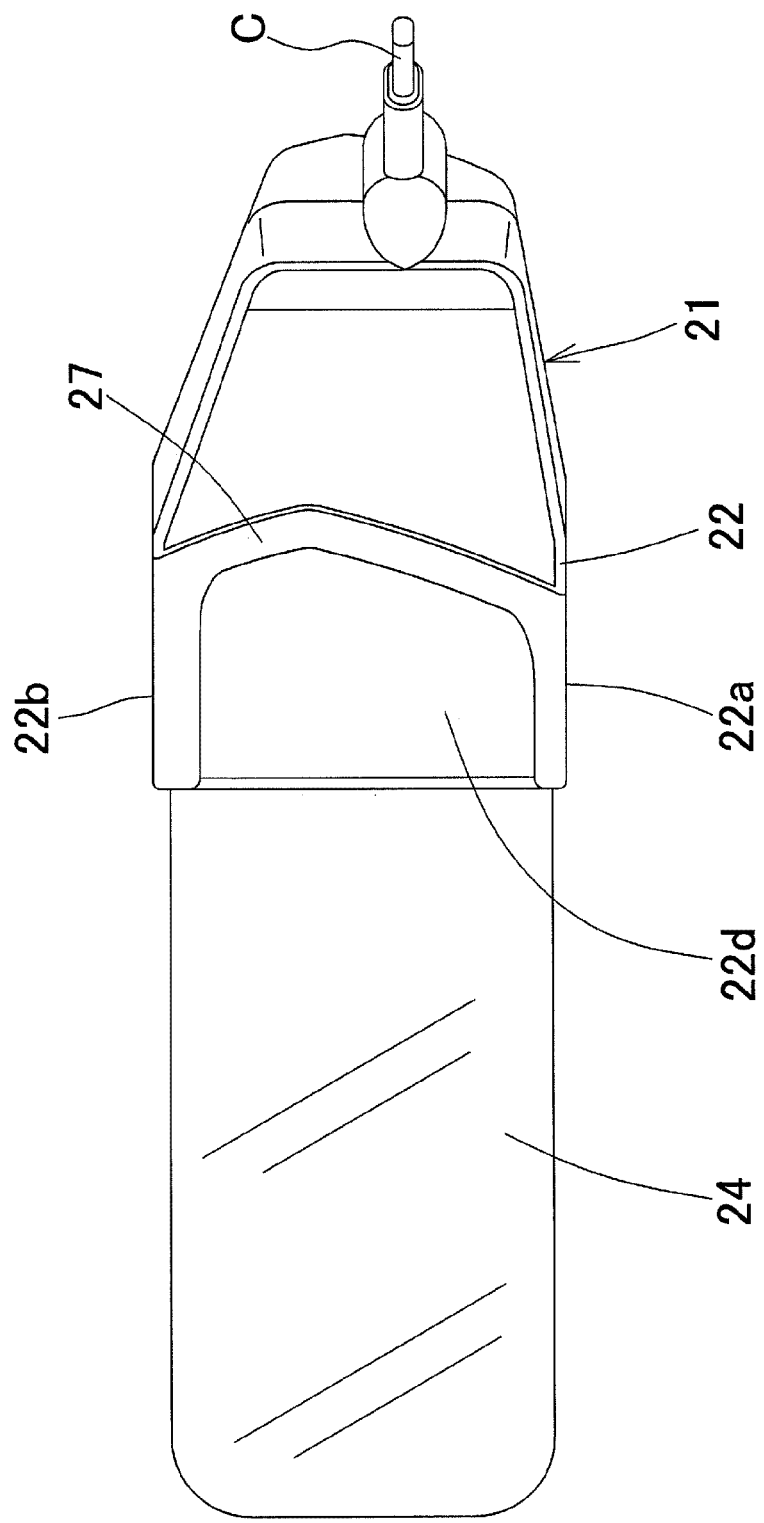
FIG. 10 is a rear view of the wearable device illustrated in FIG. 9.

Hereinafter, a first embodiment of a case in which a holding tool for a wearable device of the present invention is provided in a face or head-mounted implement that is glasses will be described in detail with reference to the drawings.

The front-rear direction, the right-left direction, the upper-lower direction, and the like in the following description are based on a state in which a user wears the face or head-mounted implement.

The glasses illustrated in FIGS. 1 to 8 are used for dust prevention, and include a lens body part 1 and temple parts 2. The illustrated lens body part 1 includes a lens 3 located in front of eyes, and a peripheral wall 4 extending so as to come into contact with a face from a whole periphery of this lens 3, and integrally molded by injection molding or the like by synthetic resin. This peripheral wall 4 is formed from an upper wall 4a, a lower wall 4b, and both side walls 4c, 4c. The temple parts 2 are formed on both ends of a frame 5 attached to the upper wall 4a of the peripheral wall 4 of the lens body part 1, formed in a twisting form extending rearward with angle adjusters A and hinges H interposed between the temple parts and the both ends as necessary, and formed with ear pad parts 2a in rear ends. In a case in which glasses are used as the face or head-mounted implement of the present invention, parts enabling the lens body part 1 to be worn on a face are not limited to the temple parts 2, and a belt may be provided as the part enabling the lens body part 1 to be worn on a face, instead of these temple parts 2. The lens body part 1 is a single-lens, but may be a twin-lens.

The holding tool for a wearable device according to this embodiment is provided in one side end of the lens body part 1, and is provided in a portion of the lens body part 1, the portion formed by cutting out or removing the side wall 4c of the lens body part 1, or molding in such a shape. That is, this holding tool is a holding frame body 11 having an upper frame part 11a, a lower frame part 11b, a front frame part 11c, and a rear frame part 11d, an end of the upper frame part 11a is connected to an end of the upper wall 4a of the lens body part 1, an end of the lower frame part 11b is connected to an end of the lower wall 4b of the lens body part 1, and an end of the front frame part 11c is connected to an end of the lens 3 of the lens body part 1, so that the holding tool is provided in one side end of the lens body part 1. A body part 22 of a wearable device 21 is detachably attached to the holding frame body 11 of this holding tool, and a display part 24 of this wearable device 21 is disposed on the inner side of the lens 3. The holding frame body 11 is a rectangular frame body composed of the upper frame part 11a, the lower frame part 11b, the front frame part 11c, and the rear frame part 11d, in the illustration. In a case in which the holding frame body 11 is a rectangular frame, such a holding frame body is versatile, an elastic pressing body 13 described below is easily provided, and operability of the elastic pressing body 13 is improved. However, the holding frame body 11 may be a polygonal frame body such as a pentagonal frame, a hexagonal frame, and an octagonal frame, an oblong frame body, or the like. In a case in which the holding frame body 11 is a frame body other than the rectangular frame, the upper frame part 11a, the lower frame part 11b, the front frame part 11c, and the rear frame part 11d means an upper region portion, a lower region portion, a front region portion, and a rear region portion in the frame body shape. Meaning of each term of the upper frame part 11a, the lower frame part 11b, the front frame part 11c, and the rear frame part 11d is similar in the following embodiments.

Now, a second embodiment of a case in which a holding tool for a wearable device of the present invention is provided in a face or head-mounted implement that is glasses will be described in detail with reference to the drawings.

The glasses illustrated in FIGS. 12 to 19 are used for dust prevention, and includes a lens body part 1 and temple parts 2 similarly to the aforementioned first embodiment, and configurations of the lens body part 1 and the temple parts 2 are similar to those of the aforementioned first embodiment, and therefore detailed description thereof will be omitted.

The holding tool for a wearable device according to this embodiment is provided in one side end of the lens body part 1, and is provided in a portion of the lens body part 1, the portion formed by cutting out or removing the side wall 4c of the lens body part 1, or molding in such a shape. That is, this holding tool is a holding frame body 11 having an upper frame part 11a, a lower frame part 11b, a front frame part 11c, and a rear frame part 11d, an upper end of the rear frame part 11d is connected to an end of the upper wall 4a of the lens body part 1, a lower end of the rear frame part 11d is connected to an end of the lower wall 4b of the lens body part 1, a front end of the rear frame part 11d is connected to an end of a lens 3 of the lens body part 1, so that the holding tool is provided in one side end of the lens body part 1. A body part 22 of a wearable device 21 is detachably attached to the holding frame body 11 of this holding tool, and a display part 24 of this wearable device 21 is disposed on the outer side of the lens 3.

Furthermore, a third embodiment of a case in which a holding tool for a wearable device of the present invention is provided in a face or head-mounted implement that is glasses will be described in detail with reference to the drawings.

Figure 20:
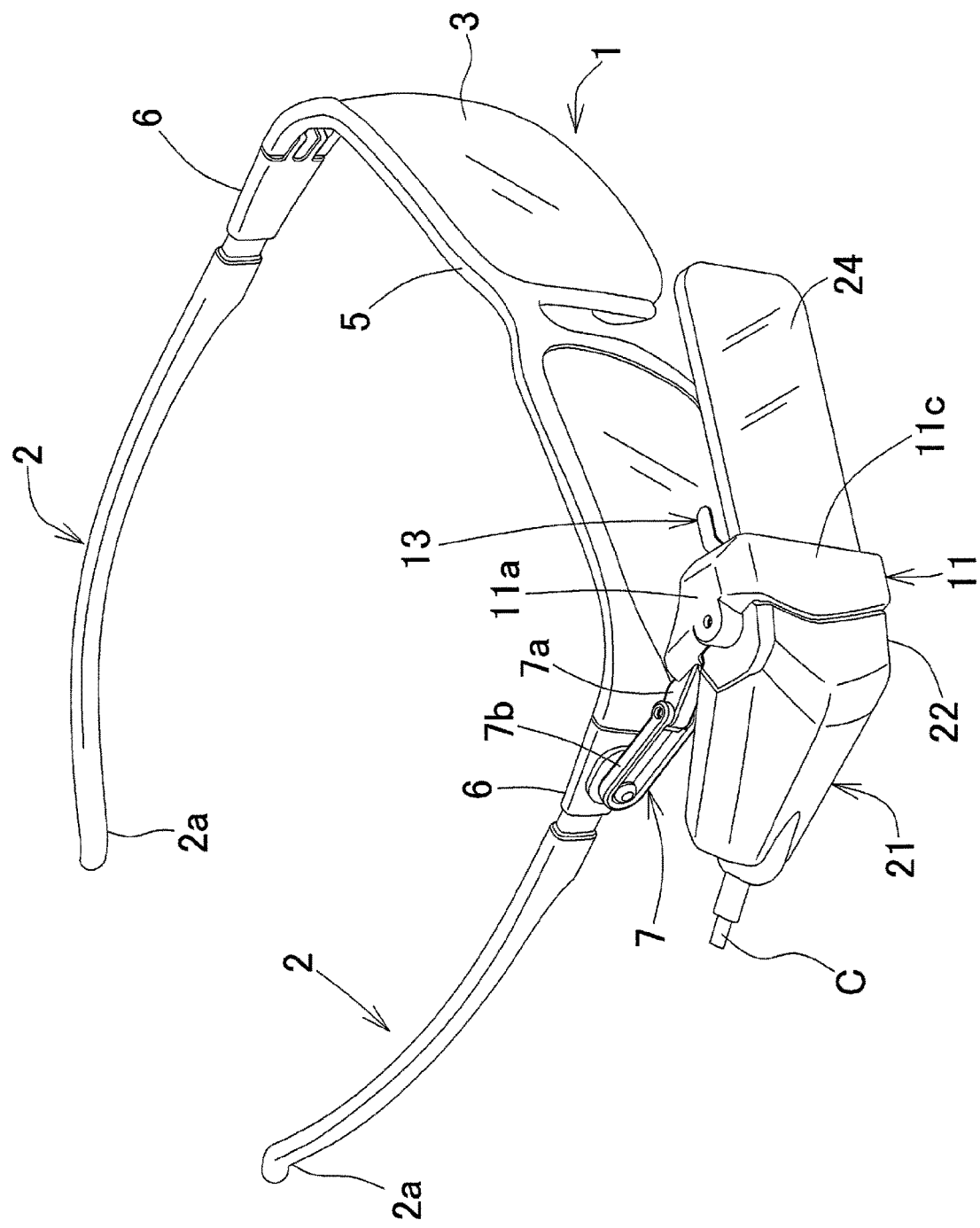
FIG. 20 is a perspective view illustrating a third embodiment in which a holding tool of the present invention is provided in a face or head-mounted implement which is glasses.
Figure 21:
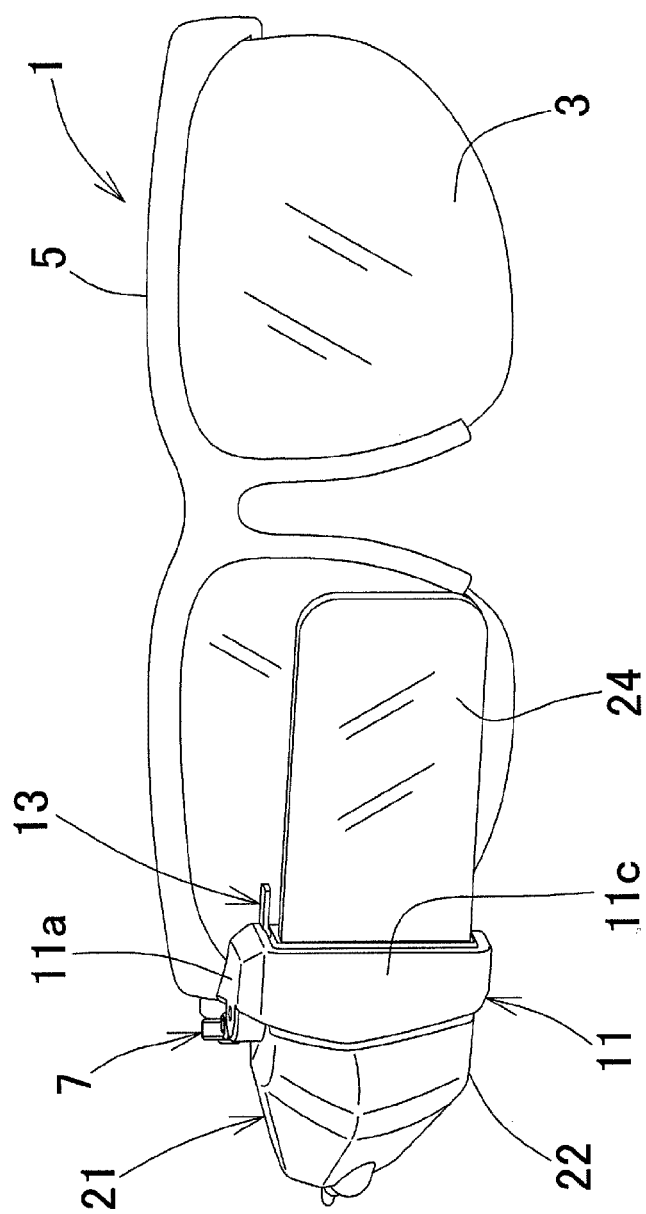
FIG. 21 is a front view of the face or head-mounted implement illustrated in FIG. 20.
Figure 22:
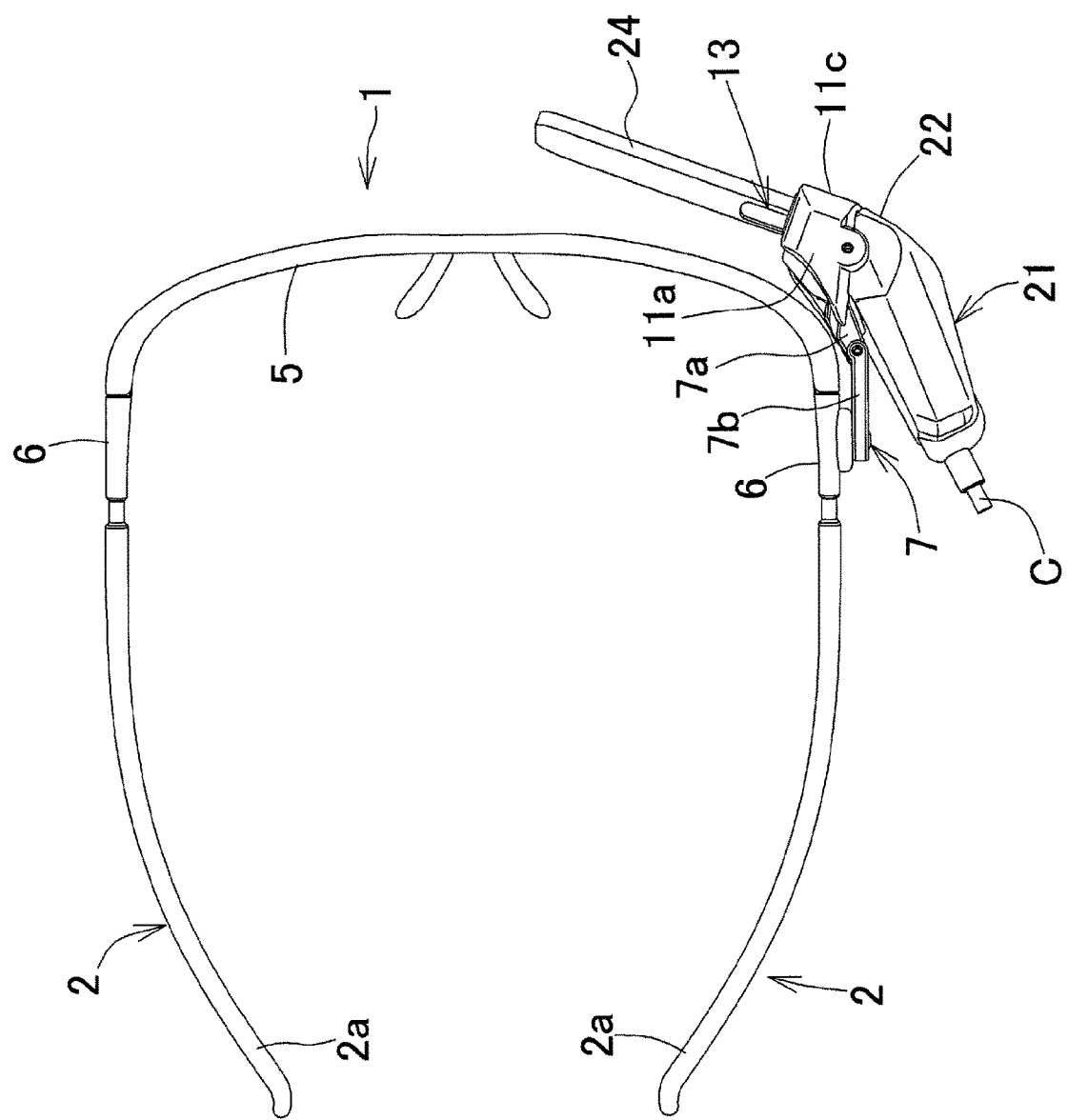
FIG. 22 is a plan view of the face or head-mounted implement illustrated in FIG. 20.

The glasses illustrated in FIGS. 20 to 22 are for general use, and includes a lens body part 1 and temple parts 2. The illustrated lens body part 1 includes lenses 3 located in front of eyes, and a frame 5 holding the lenses 3. The temple parts 2 are formed on both ends of the frame 5, formed in a twisting form extending rearward with wraparound endpieces 6 interposed between the temple parts and the both ends, and formed with ear pad parts 2*a* in rear ends. In a case in which glasses are used as the face or head-mounted implement of the present invention, parts enabling the lens body part 1 to be worn on a face are not limited to the temple parts 2, and a belt may be provided as the part enabling the lens body part 1 to be worn on a face like goggles, instead of these temple parts 2. The lens body part 1 is a twin-lens, but may be a single-lens or a frame only.

The holding tool for a wearable device according to this embodiment is provided in one side end of the lens body part 1, and is provided in an end of the frame 5 by using a support arm 7, or provided in the wraparound endpiece 6 of the end. That is, this holding tool is a holding frame body 11 including an upper frame part 11*a*, a lower frame part 11*b*, a front frame part 11*c*, and a rear frame part 11*d*, similarly to the glasses illustrated in the first embodiment and the second embodiment, a leading end of a front arm 7*a* of a support arm 7 in which the front arm 7*a* and a rear arm 7*b* are pivotally supported so as to freely adjust the respective angles is fixed to the rear frame part 11*d* of the holding frame body 11, and a rear end of the rear arm 7*b* of this support arm 7 is pivotally supported on an end of the frame 5 of the lens body part 1, or on the wraparound endpiece 6 of the end, so that the holding tool is provided in one side end of the lens body part 1. A body part 22 of a wearable device 21 is detachably attached to the holding frame body 11 of this holding tool, and a display part 24 of this wearable device 21 is disposed on the outer side of the lens 3

A fourth embodiment of a case in which a holding tool for a wearable device of the present invention is provided in a face or head-mounted implement that is a head band will be described in detail with reference to the drawings.

Figure 23:
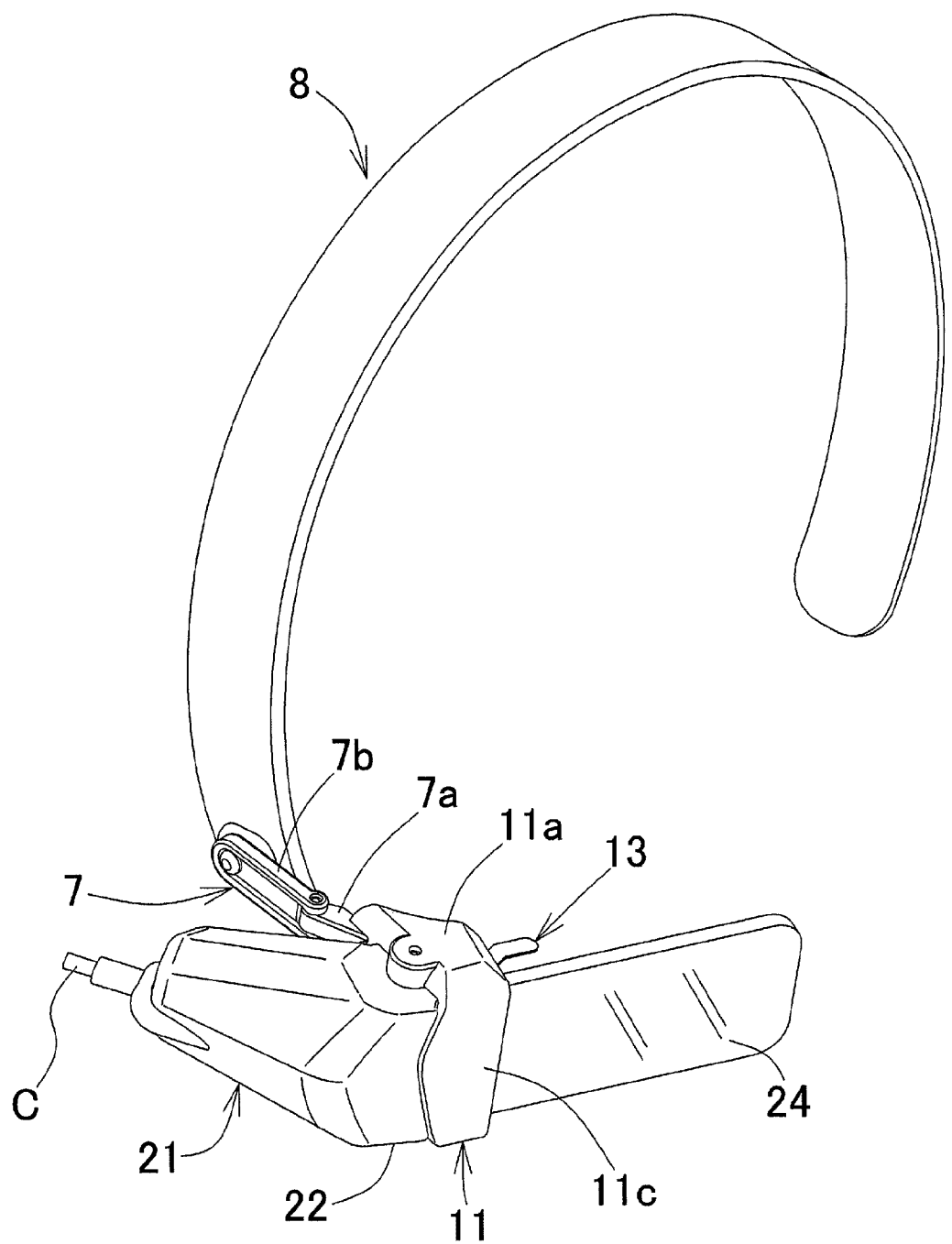
FIG. 23 is a perspective view illustrating a fourth embodiment in which a holding tool of the present invention is provided in a face or head-mounted implement which is a head band.
Figure 24:
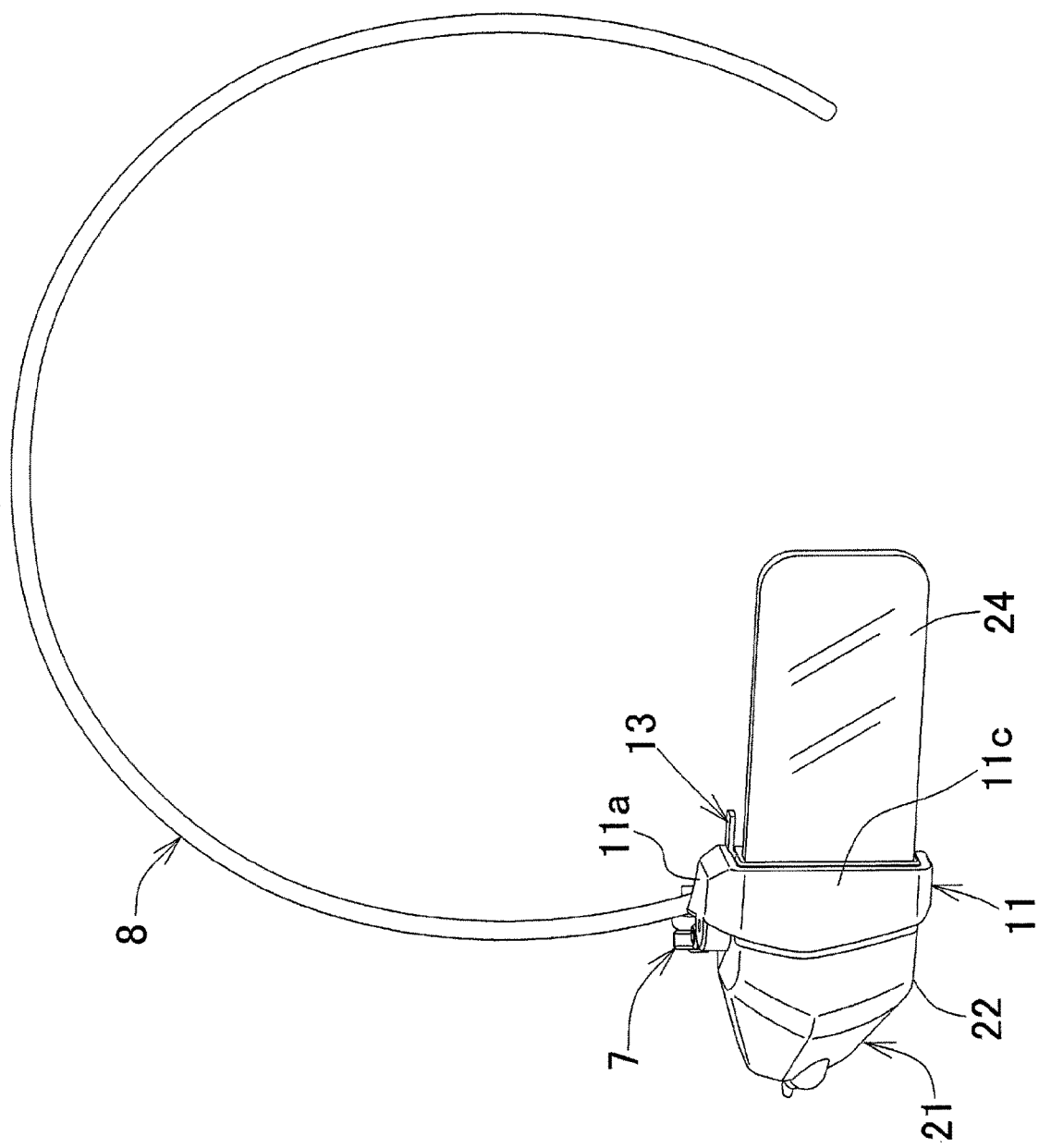
FIG. 24 is a front view of the face or head-mounted implement illustrated in FIG. 23.
Figure 25:
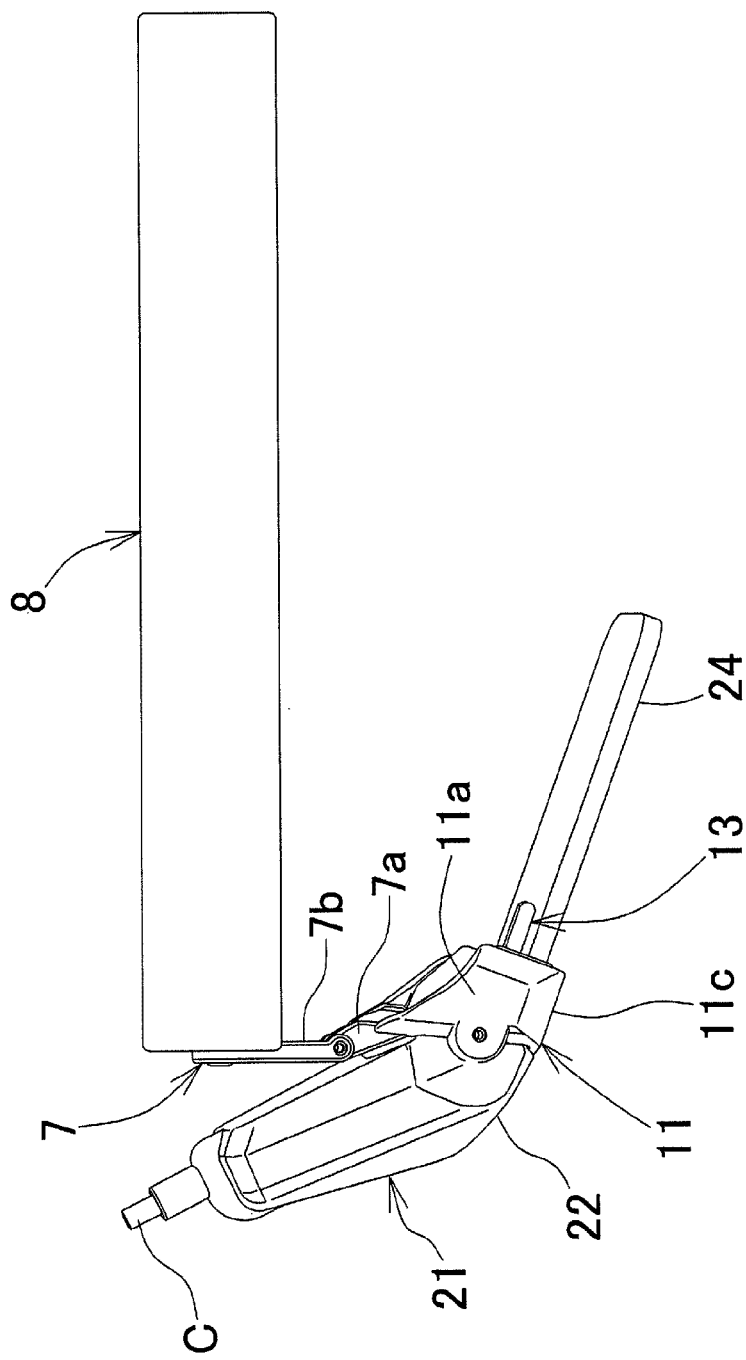
FIG. 25 is a plan view of the face or head-mounted implement illustrated in FIG. 23.

The head band illustrated in FIGS. 23 to 25 is a vertically wearing type head band, is composed of a clamping body 8 such as a synthetic resin plate formed in an inverted substantially U-shape and having elasticity, and is worn on a head such that this clamping body 8 clamps from a head top to portions right above ears of temporal parts.

The holding tool for a wearable device in this embodiment is provided in an end of the clamping body 8, and is provided in the end of the clamping body 8 by using the support arm 7. That is, this holding tool is a holding frame body 11 including an upper frame part 11*a*, a lower frame part 11*b*, a front frame part 11*c*, and a rear frame part 11*d*, similarly to the glasses illustrated in the first embodiment and the second embodiment, a leading end of a front arm 7*a* of a support arm 7 in which the front arm 7*a* and a rear arm 7*b* are pivotally supported so as to freely adjust the respective angles is fixed to the rear frame part 11*d* of the holding frame body 11, and a rear end of the rear arm 7*b* of this support arm 7 is pivotally supported on an end of the clamping body 8, so that the holding tool is a holding frame body 11 is provided in one end of the clamping body 8. The body part 22 of the wearable device 21 is detachably attached to the holding frame body 11 of this holding tool, and a display part 24 of this wearable device 21 is disposed in a region where a head band wearer can see a display part 24 of this wearable device 21.

A fifth embodiment of a case in which a holding tool for a wearable device of the present invention is provided in a face or head-mounted implement that is a helmet will be described in detail with reference to the drawings.

Figure 26:
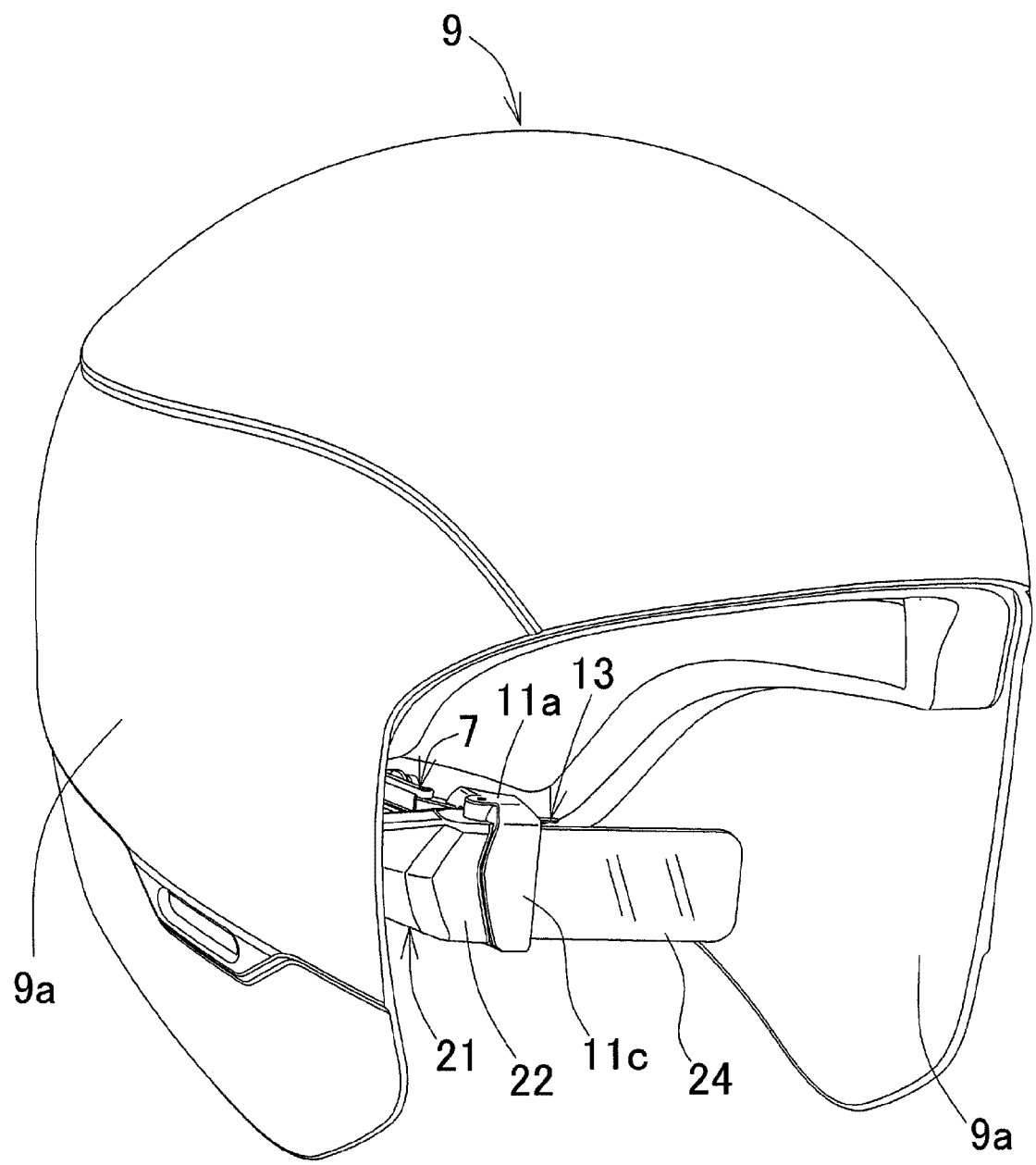
FIG. 26 is a perspective view illustrating a fifth embodiment in which a holding tool of the present invention is provided in a face or head-mounted implement which is a helmet.
Figure 27:
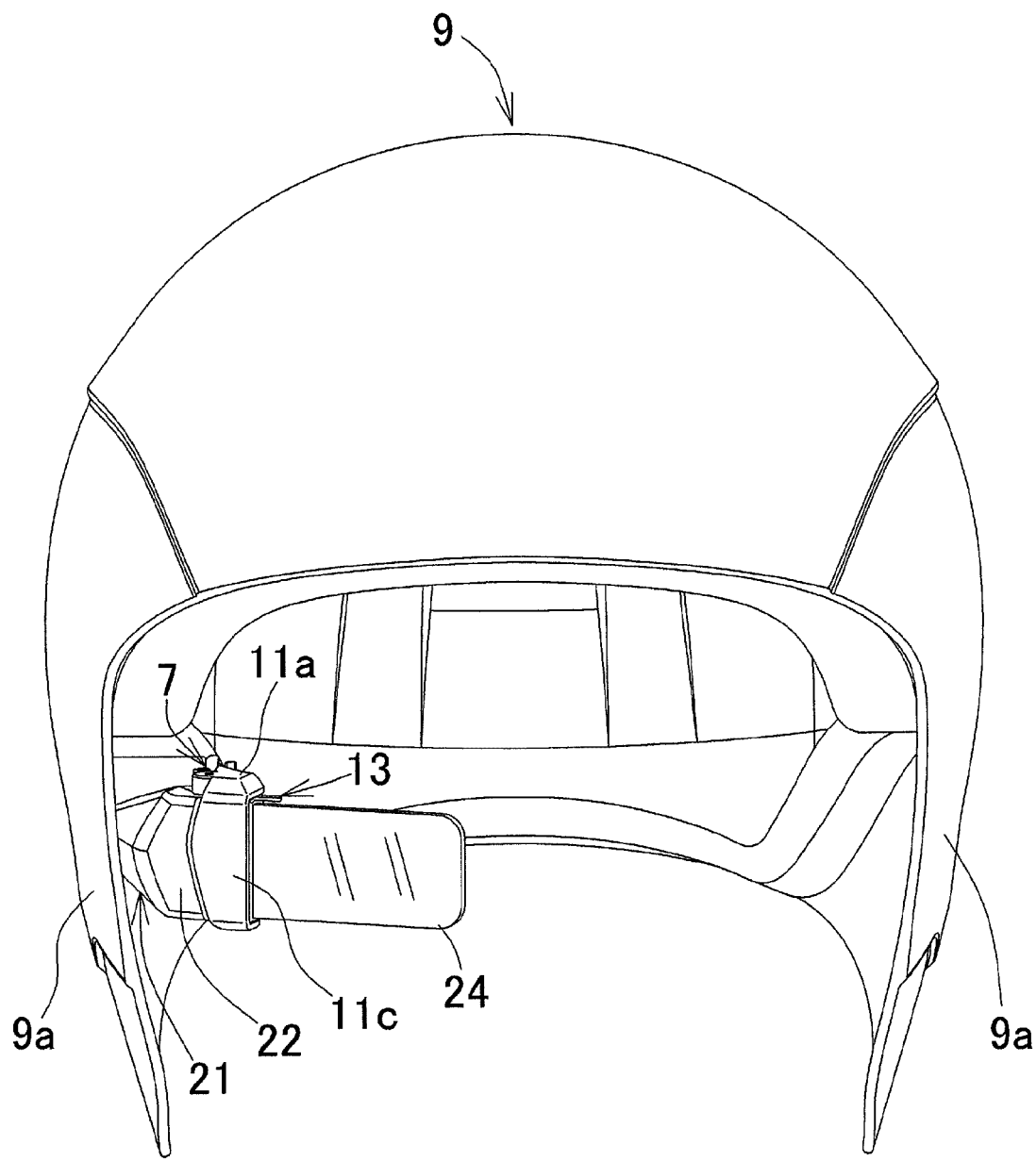
FIG. 27 is a front view of the face or head-mounted implement illustrated in FIG. 26.
Figure 28:
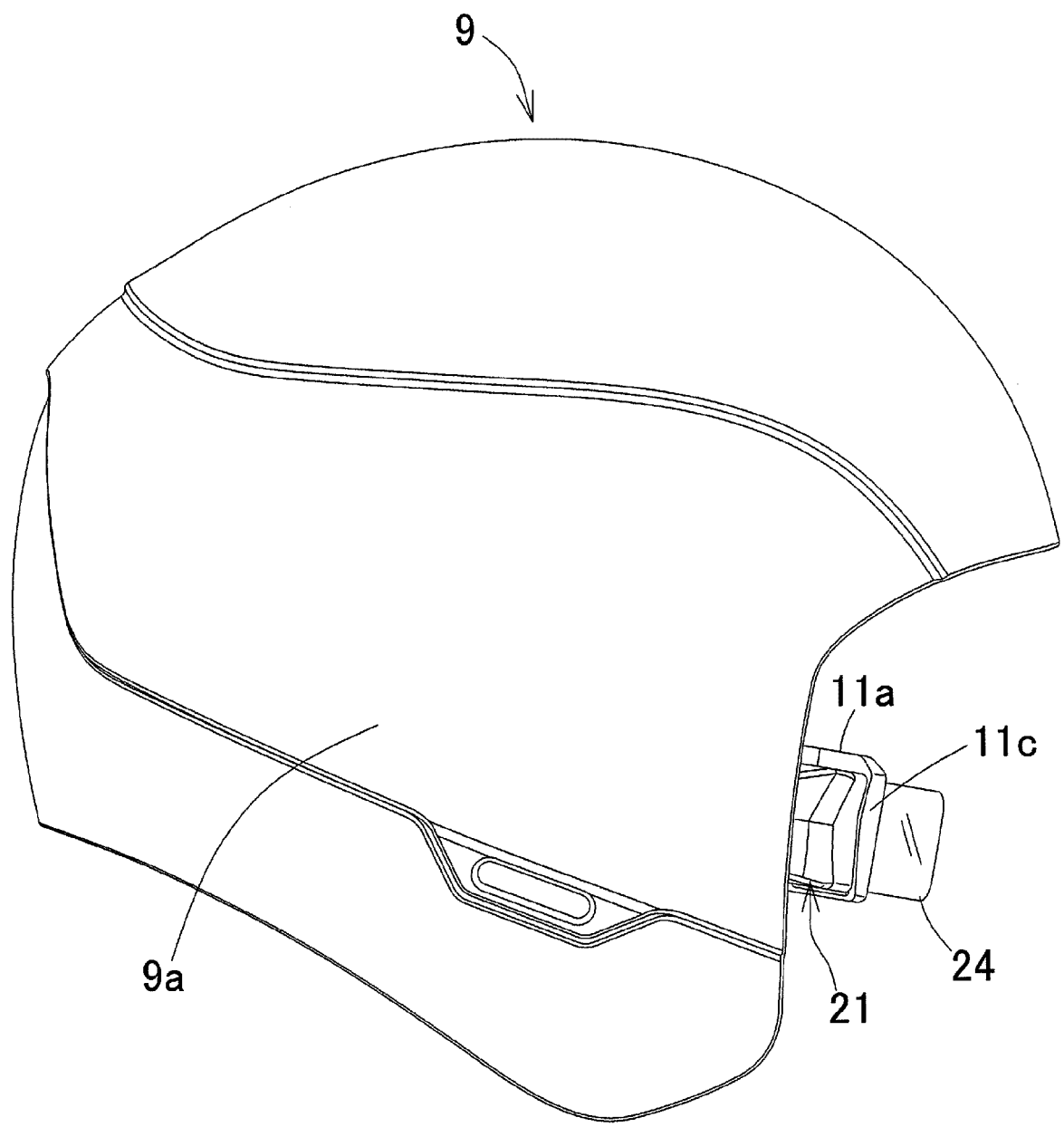
FIG. 28 is a side view of the face or head-mounted implement illustrated in FIG. 26.
Figure 29:
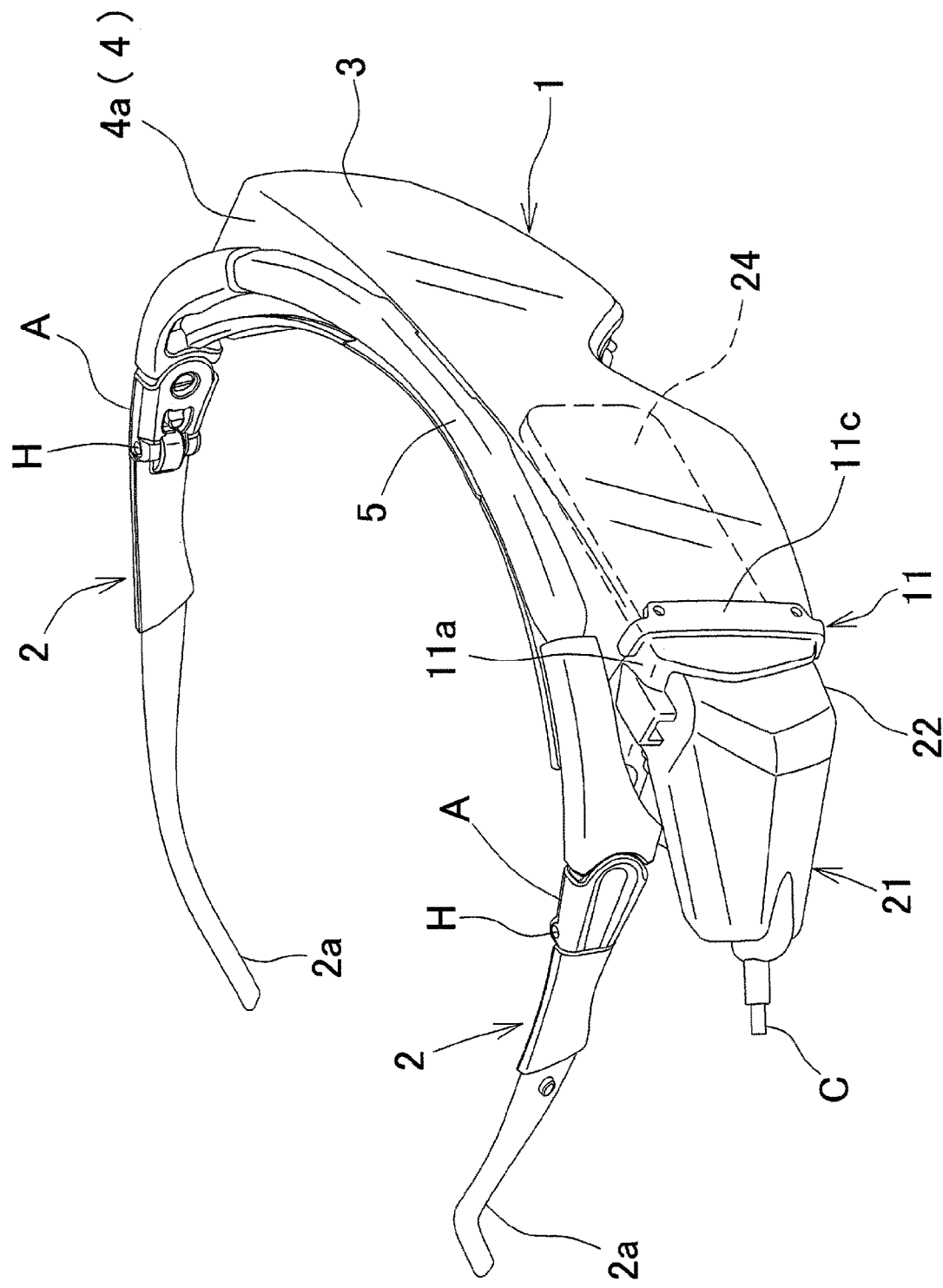
FIG. 29 is a perspective view illustrating a sixth embodiment in which a holding tool of the present invention is provided in a face or head-mounted implement which is glasses.
Figure 30:
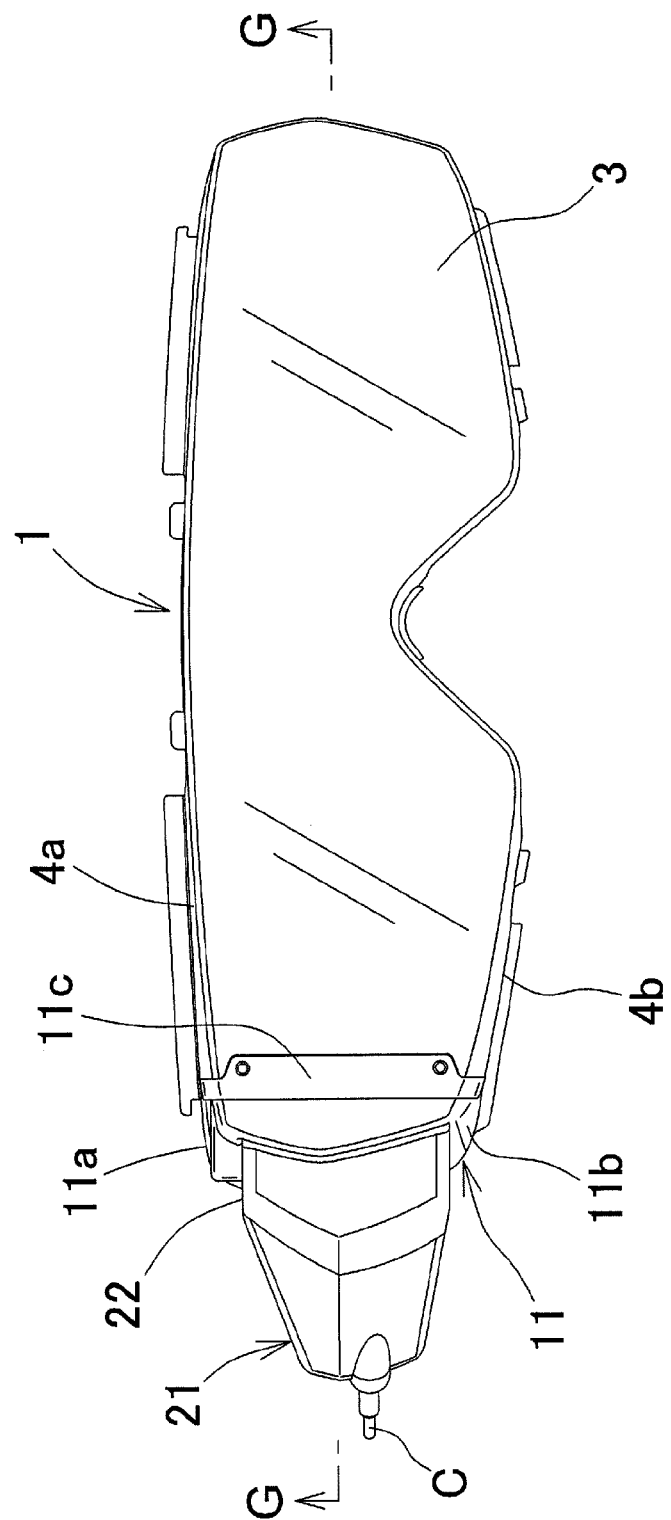
FIG. 30 is a front view of a main part of the face or head-mounted implement illustrated in FIG. 29.
Figure 31:
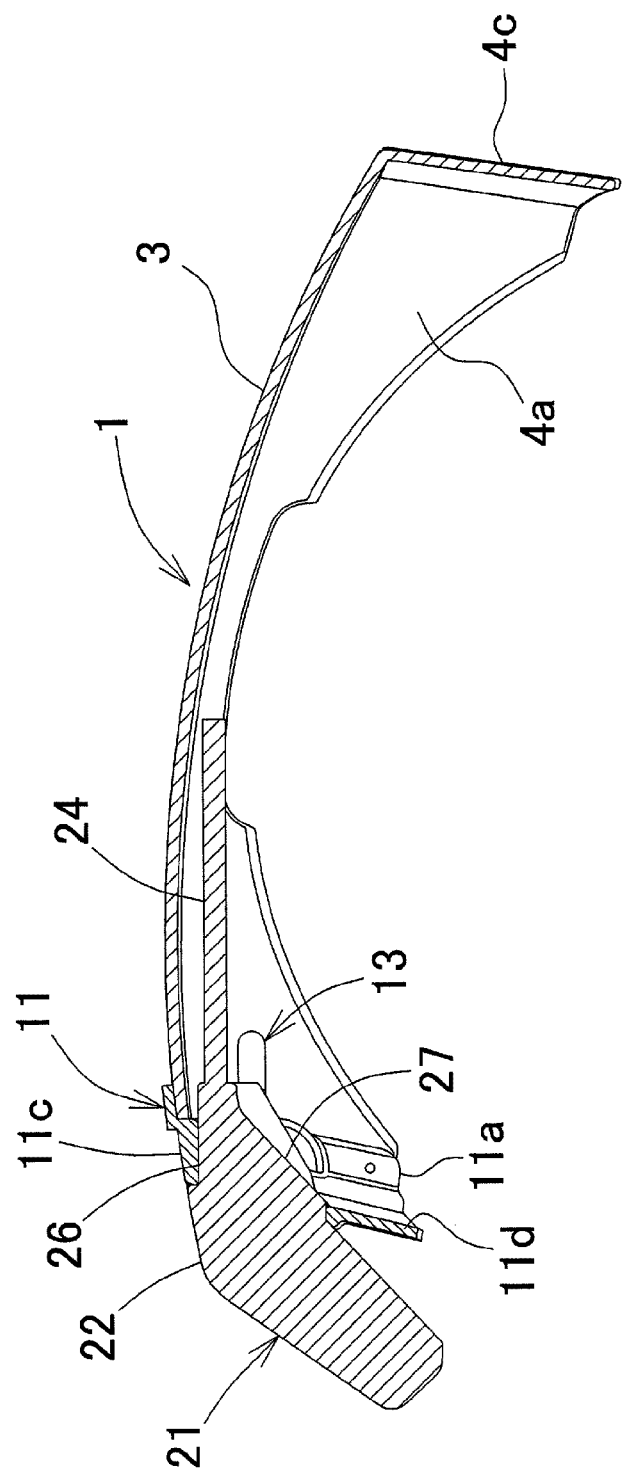
FIG. 31 is a sectional view taken along the line G-G in FIG. 29.
Figure 32:
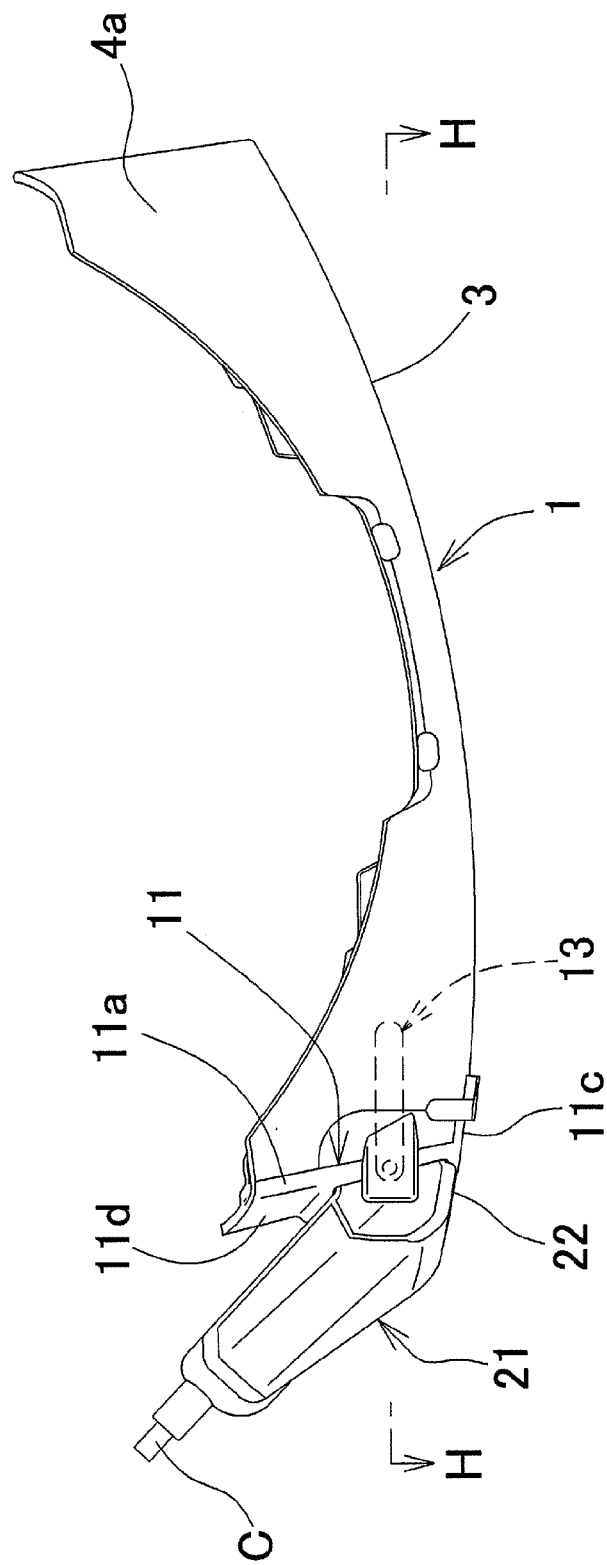
FIG. 32 is a plan view of the main part of the face or head-mounted implement illustrated in FIG. 29.
Figure 33:
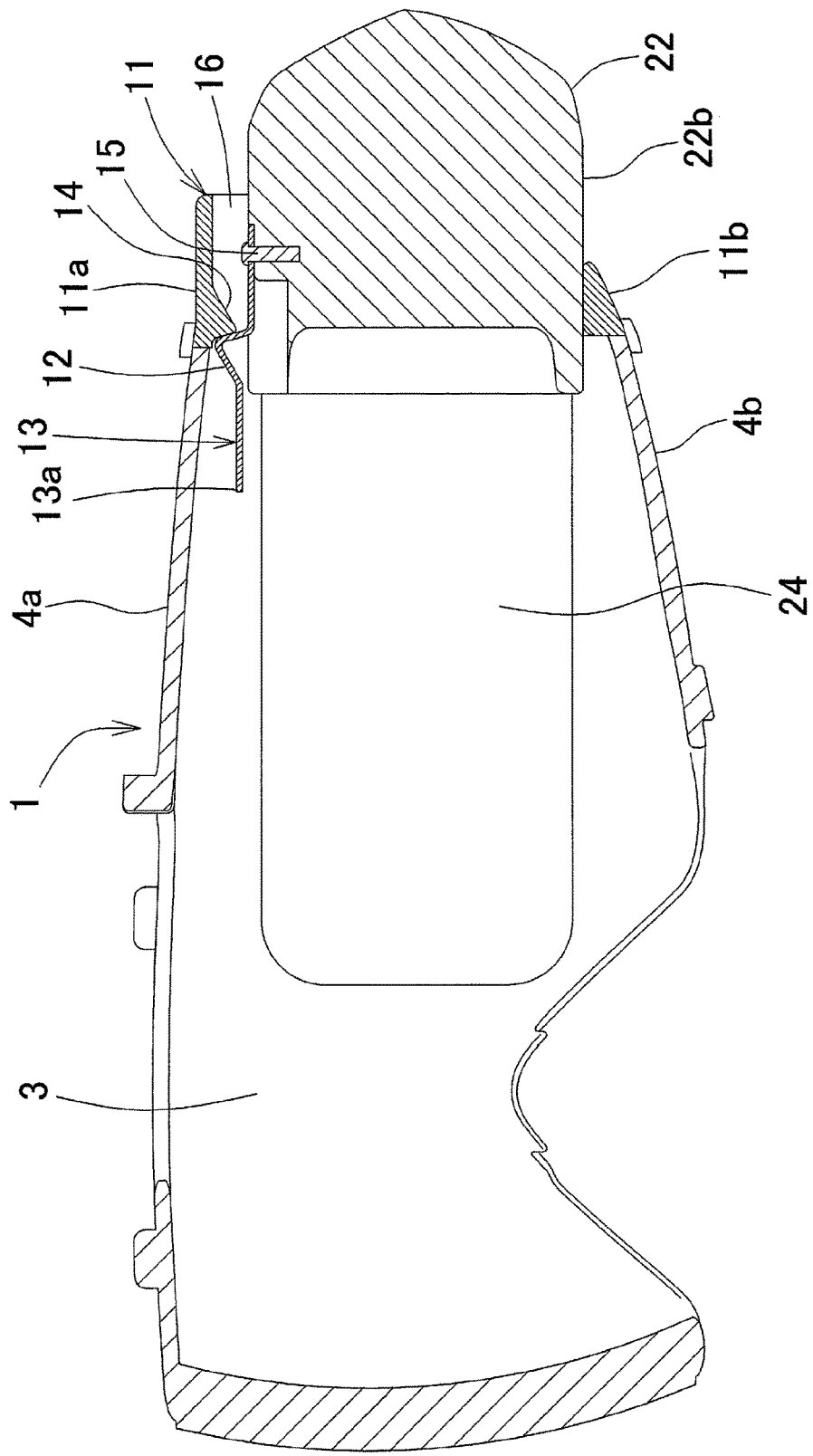
FIG. 33 is a sectional view taken along the line H-H in FIG. 32.
Figure 34:
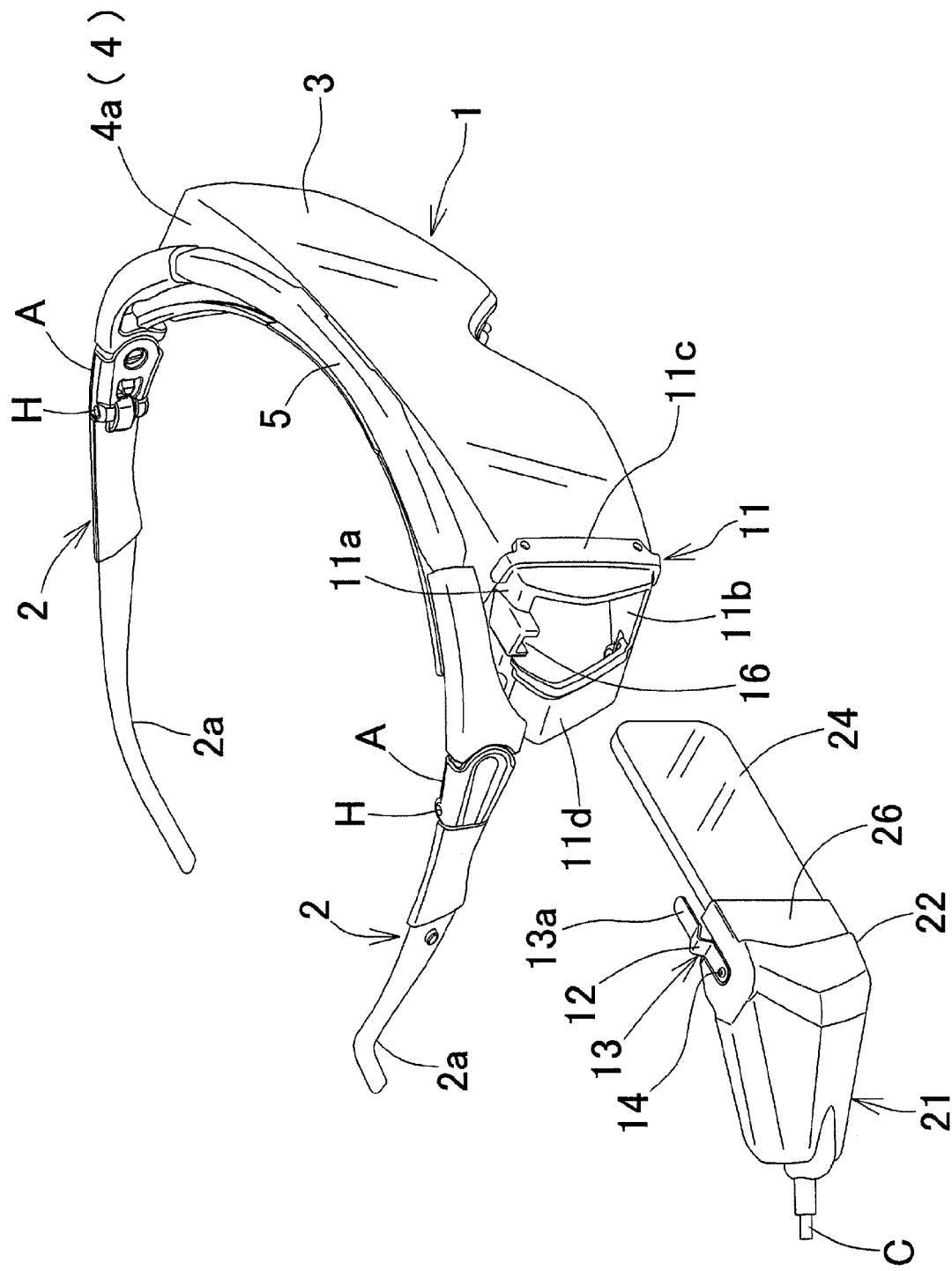
FIG. 34 is a perspective view in a state in which a wearable device is detached from the face or head-mounted implement illustrated in FIG. 29.
Figure 35:
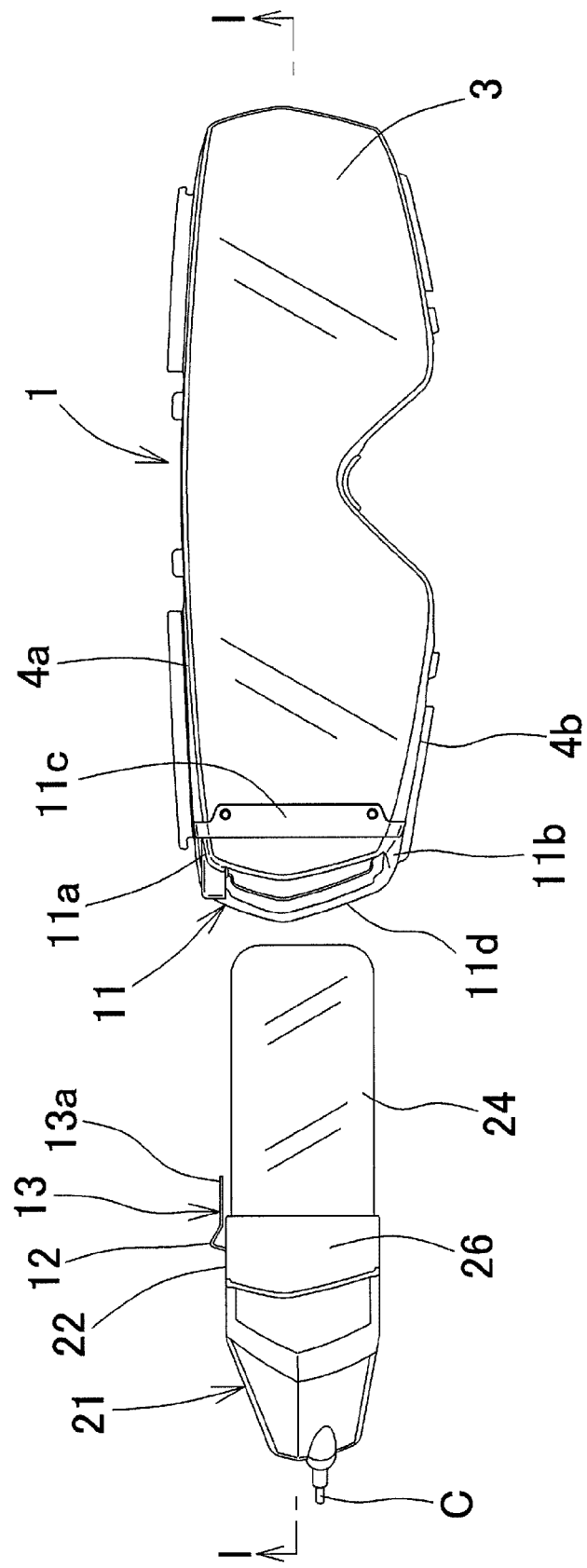
FIG. 35 is a front view of the main part of the face or head-mounted implement in a state illustrated in FIG. 34.
Figure 36:
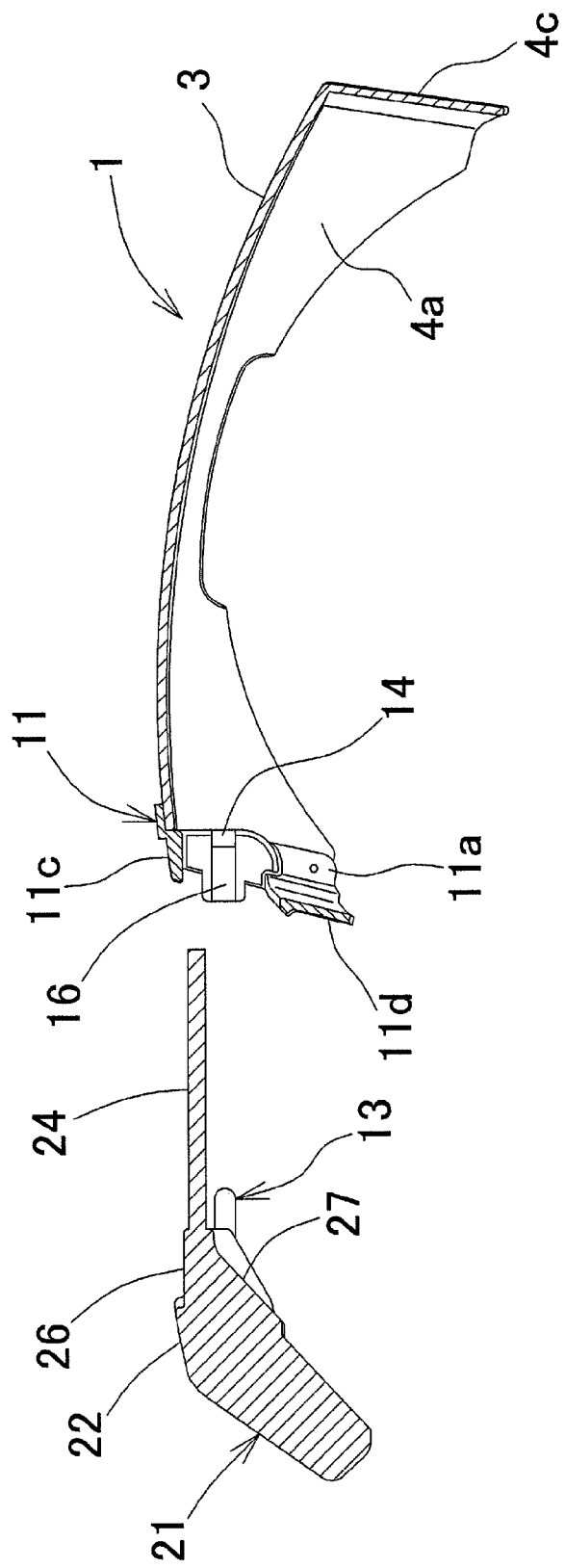
FIG. 36 is a sectional view taken along the line I-I in FIG. 35.
Figure 37:
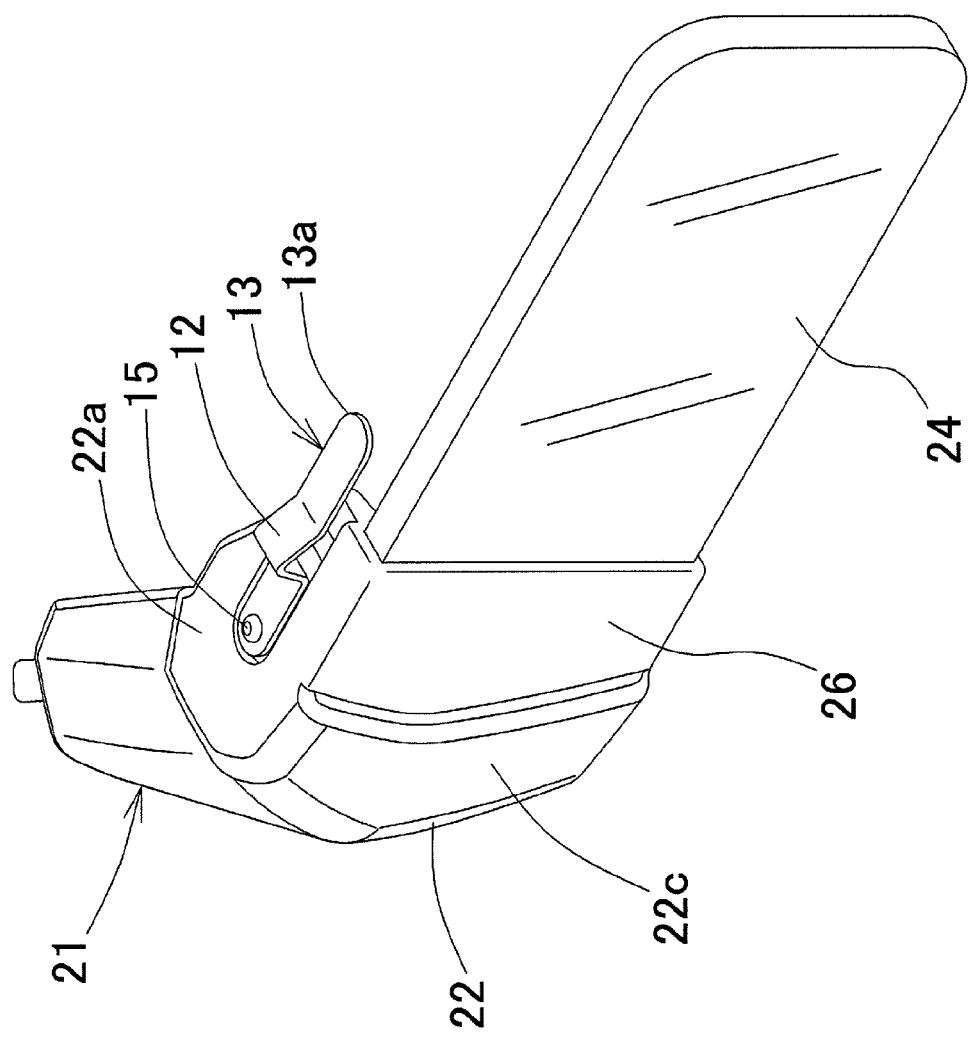
FIG. 37 is a perspective view of the wearable device detachably attached to the holding tool of the present invention.
Figure 38:
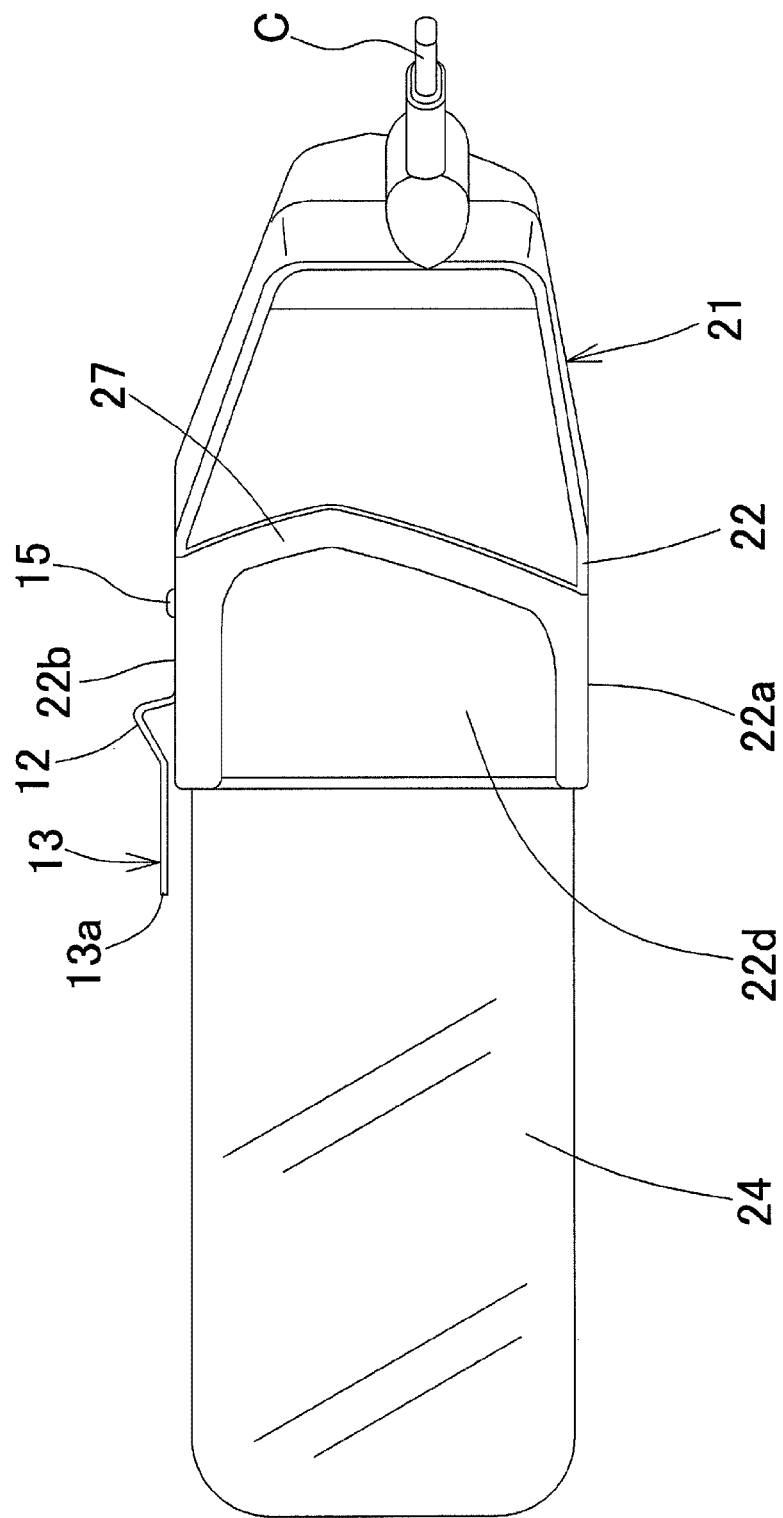
FIG. 38 is a rear view of the wearable device illustrated in FIG. 37.

The helmet illustrated in FIGS. 26 to 28 is a jet type helmet, and a front opening and a bottom opening are provided in a shell 9 forming an outer shell of the helmet, and both sides of the shell 9 are cheek side parts 9*a*.

The holding tool for a wearable device in this embodiment is provided on the inner side of the cheek side part 9*a* on one side of the shell 9. That is, this holding tool is a holding frame body 11 including an upper frame part 11*a*, a lower frame part 11*b*, a front frame part 11*c*, and a rear frame part 11*d*, similarly to the glasses illustrated in the first embodiment and the second embodiment, a leading end of a front arm 7*a* of a support arm 7 in which the front arm 7*a* and a rear arm 7*b* are pivotally supported so as to freely adjust the respective angles is fixed to the rear frame part 11*d* of the holding frame body 11, and a rear end of the rear arm 7*b* of this support arm 7 is pivotally supported on the inner side of the cheek side part 9*a* on one side of the shell 9, so that the holding tool is provided on the inner side of the cheek side part 9*a* on one side of the shell 9, similarly to the glasses illustrated in the third embodiment and the head band illustrated in the fourth embodiment. In the holding tool, a part having the same structure may be provided on the outer side of the cheek side part 9*a* on one side of the shell 9. The body part 22 of the wearable device 21 is detachably attached to the holding frame body 11 of this holding tool, and a display part 24 of this wearable device 21 is disposed in a region where a helmet wearer can see a display part 24 of this wearable device 21.

Now, a sixth embodiment of a case in which a holding tool for a wearable device of the present invention is provided in a face or head-mounted implement that is glasses will be described in detail with reference to the drawings.

The glasses illustrated in FIGS. 29 to 36 are used for dust prevention, and includes a lens body part 1 and temple parts 2. The illustrated lens body part 1 includes lens 3 located in front of eyes, and a peripheral wall 4 extending so as to come into contact with a face from a whole periphery of this lens 3, and integrally molded by injection molding or the like by synthetic resin. This peripheral wall 4 is formed from an upper wall 4*a*, a lower wall 4*b*, and both side walls 4*c*, 4*c*. The temple parts 2 are formed on both ends of a frame 5 attached to the upper wall 4*a* of the peripheral wall 4 of the lens body part 1, formed in a twisting form extending rearward with angle adjusters A and hinges H interposed between the temple parts and the both ends as necessary, and formed with ear pad parts 2*a* in rear ends. In a case in which glasses are used as the face or head-mounted implement of the present invention, parts enabling the lens body part 1 to be worn on a face are not limited to the temple parts 2, and a belt may be provided as the part enabling the lens body part 1 to be worn on a face like goggles, instead of these temple parts 2. The lens body part 1 is a single-lens, but may be a twin-lens.

The holding tool for a wearable device according to this embodiment is provided in one side end of the lens body part 1, and is provided in a portion of the lens body part 1, the portion formed by cutting out or removing the side wall 4c of the lens body part 1, or molding in such a shape. That is, this holding tool is a holding frame body 11 having an upper frame part 11a, a lower frame part 11b, a front frame part 11c, and a rear frame part 11d, an end of the upper frame part 11a is connected to an end of the upper wall 4a of the lens body part 1, an end of the lower frame part 11b is connected to an end of the lower wall 4b of the lens body part 1, and an end of the front frame part 11c is connected to an end of the lens 3 of the lens body part 1, so that the holding tool is provided in one side end of the lens body part 1. A body part 22 of a wearable device 21 is detachably attached to the holding frame body 11 of this holding tool, and a display part 24 of this wearable device 21 is disposed on the inner side of the lens 3.

Although not illustrated, the holding tool for a wearable device in this embodiment may be provided in the one side end of the lens body part 1 of the glasses similar to the second embodiment, and the display part 24 of this wearable device 21 may be disposed on the outer side of the lens 3.

Furthermore, although not illustrated, the holding tool for a wearable device in this embodiment may be provided in the one side end of the lens body part 1 of the glasses similar to the third embodiment, and the display part 24 of this wearable device 21 may be disposed on the outer side of the lens 3.

Although not illustrated, the holding tool for a wearable device in this embodiment may be provided in the one end of the clamping body 8 of the head band similar to the fourth embodiment, and the display part 24 of the wearable device 21 may be disposed in the region where a head band wearer can see the display part 24 of the wearable device 21, or may be provided on the inner side or the outer side of the cheek side part 9a on the one side of the shell 9 of the helmet similar to the fifth embodiment, and the display part 24 of the wearable device 21 may be disposed in the region where a helmet wearer can see the display part 24 of the wearable device 21.

In the holding tool for a wearable device of the present invention described in each of the first to the fifth embodiments, the upper frame part 11a, the lower frame part 11b, the front frame part 11c, and the rear frame part 11d of the holding frame body 11 are each formed in a substantially plate shape, the flat plate shaped elastic pressing body 13 formed with a projected engagement part 12 is provided in at least one of the upper frame part 11a and the lower frame part 11b from these upper frame part 11a and lower frame part 11b toward the inside of the holding frame body 11. In the illustration, the elastic pressing body 13 is provided in the upper frame part 11a of the holding frame body 11. Furthermore, a recessed engagement part 23 detachably engaged with the projected engagement part 12 is formed in at least one of the upper surface 22a and the lower surface 22b of the body part 22 of the wearable device 21. In the illustration, the recessed engagement part 23 is formed in the upper surface 22a of the body part 22.

Figure 11:
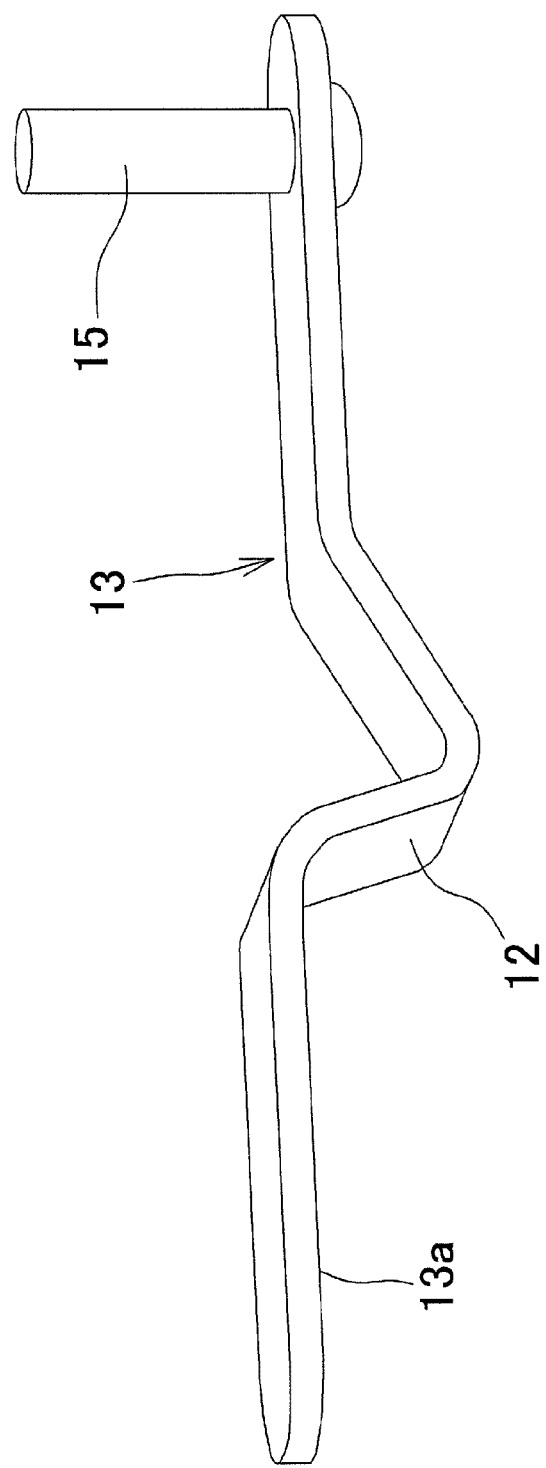
FIG. 11 is a perspective view of an elastic pressing body fixed to a holding frame body of the holding tool of the present invention.
Figure 12:
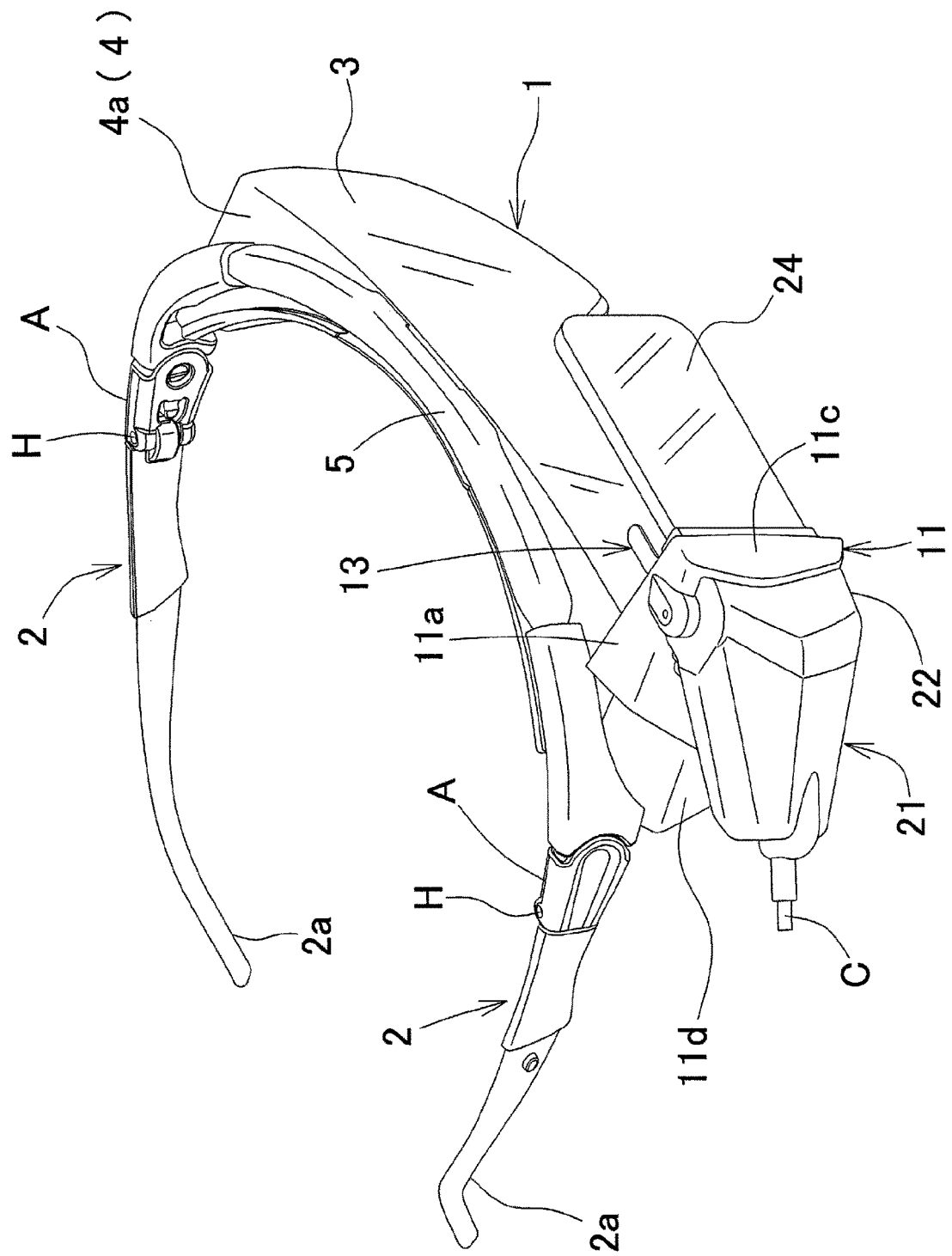
FIG. 12 is a perspective view illustrating a second embodiment in which a holding tool of the present invention is provided in a face or head-mounted implement which is glasses.
Figure 13:
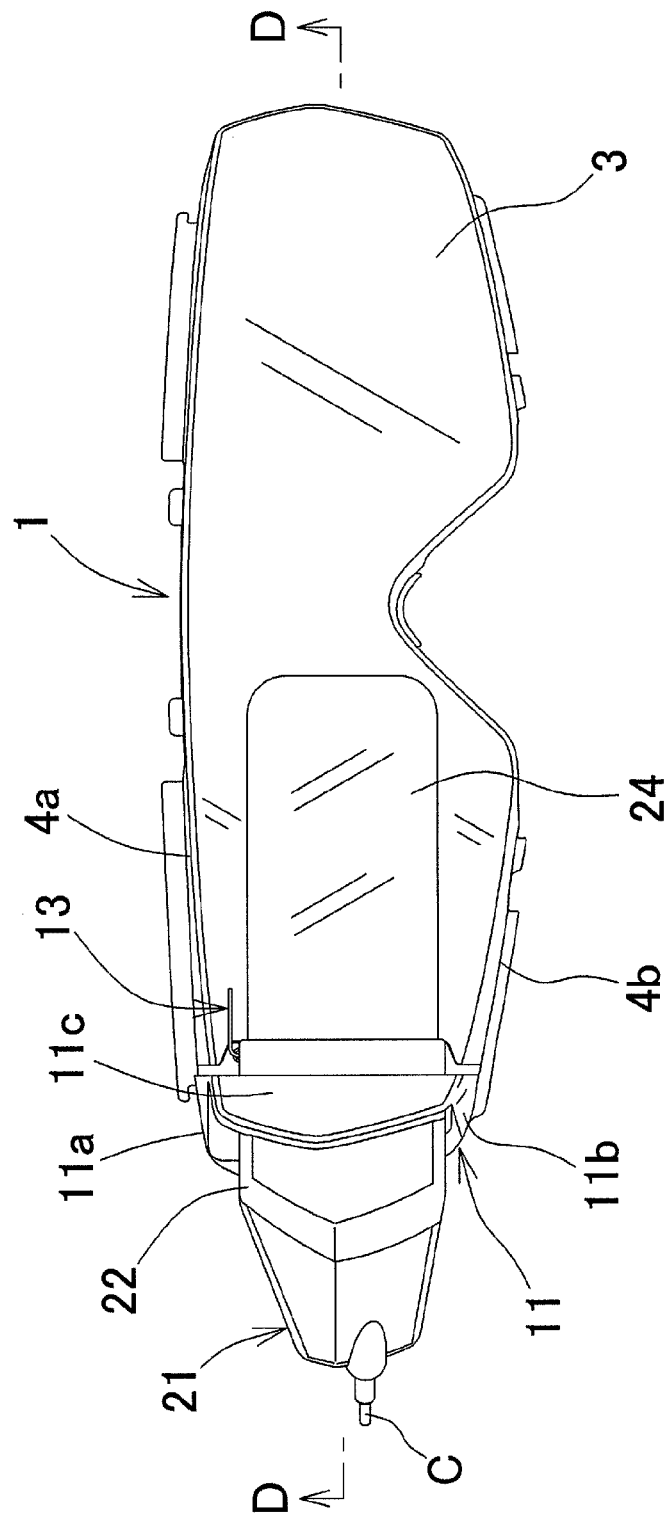
FIG. 13 is a front view of a main part of the face or head-mounted implement illustrated in FIG. 12.
Figure 14:
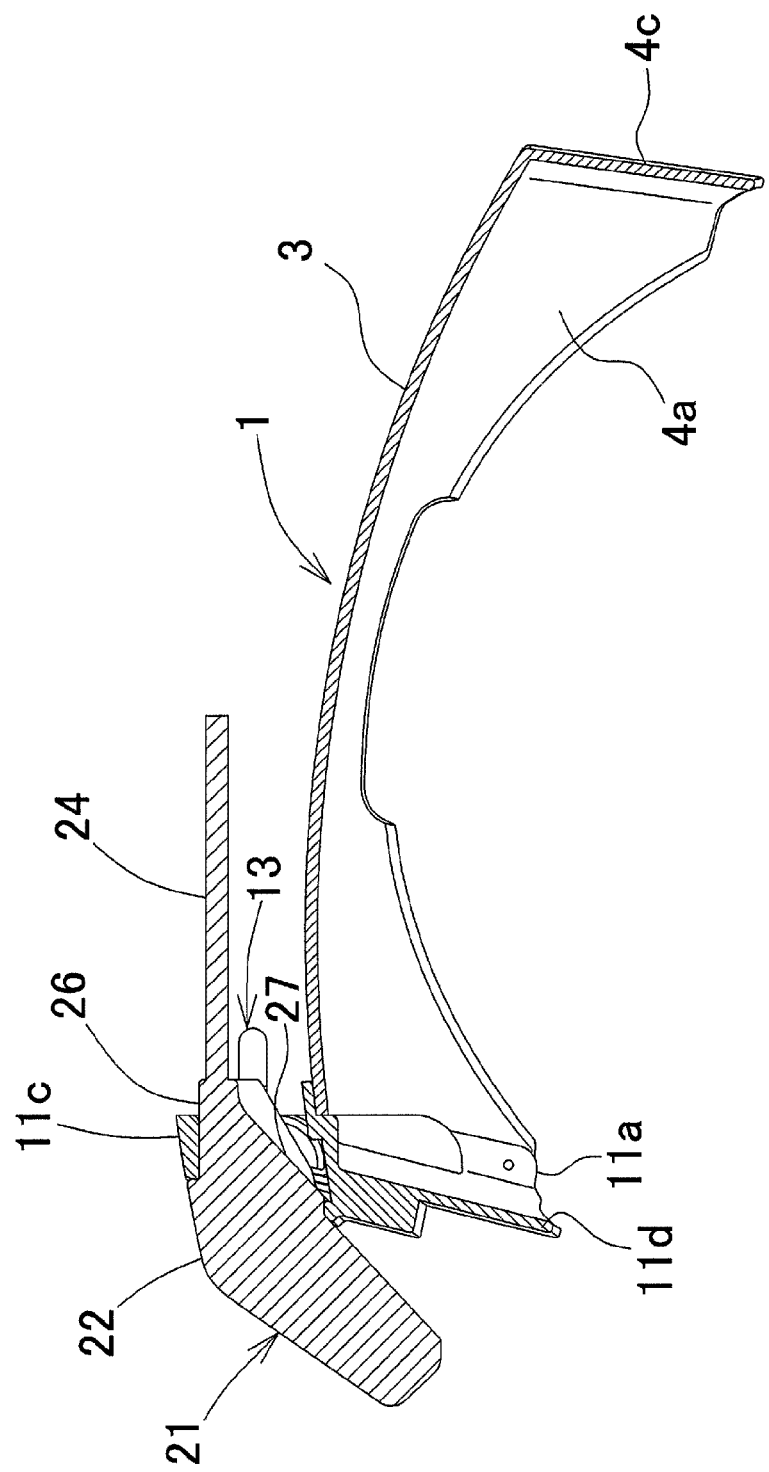
FIG. 14 is a sectional view taken along the line D-D in FIG. 13.
Figure 15:
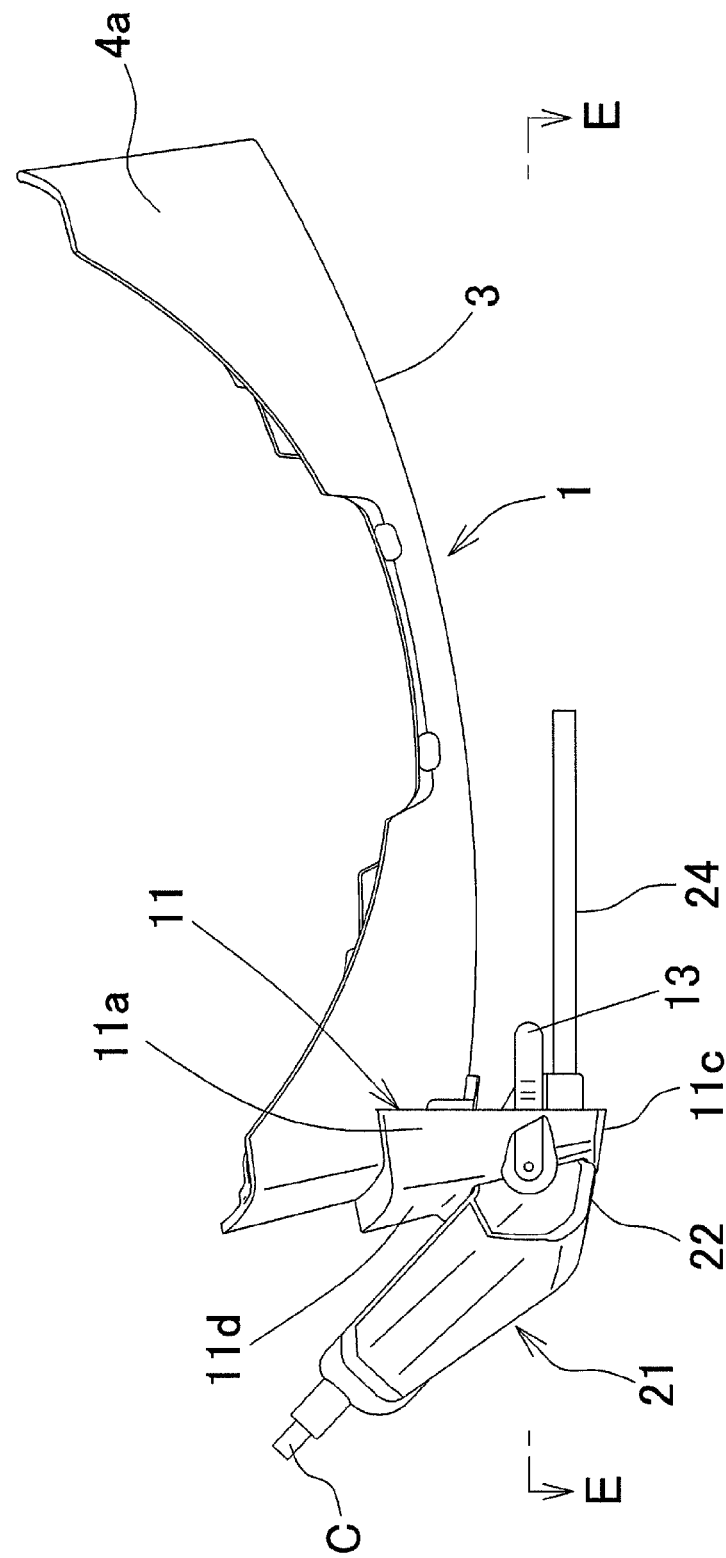
FIG. 15 is a plan view of the main part of the face or head-mounted implement illustrated in FIG. 12.
Figure 16:
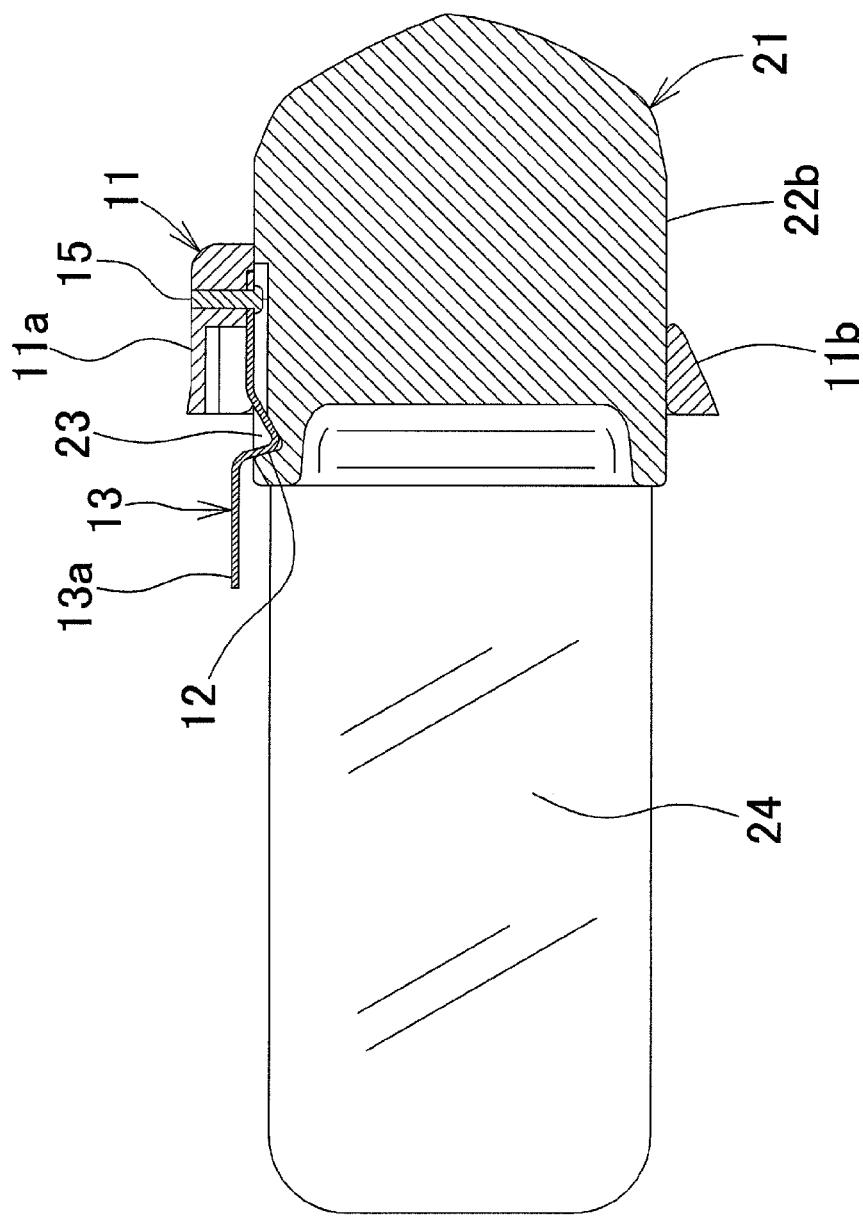
FIG. 16 is a sectional view taken along the line E-E in FIG. 15.
Figure 17:
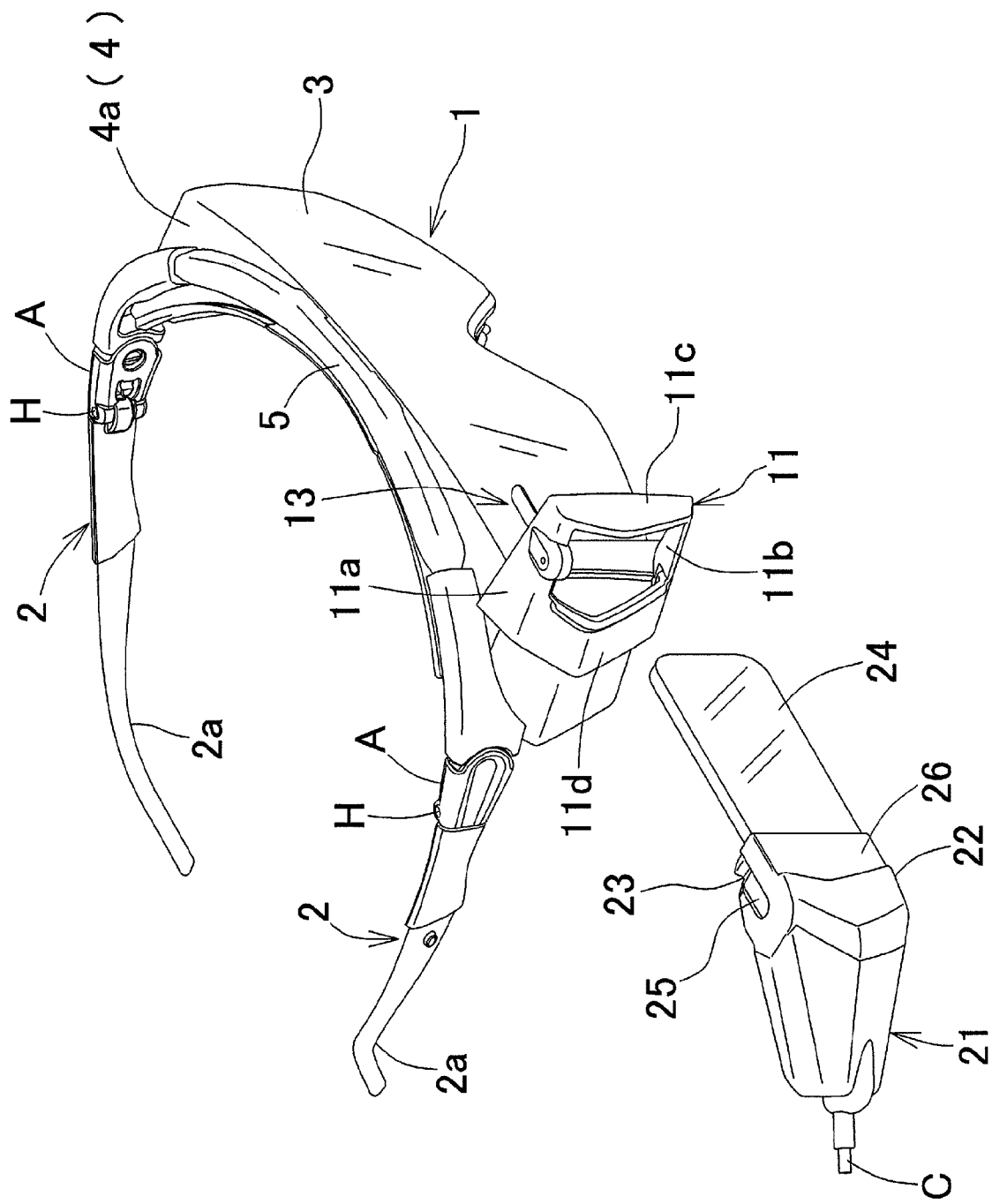
FIG. 17 is a perspective view in a state in which a wearable device is detached from the face or head-mounted implement illustrated in FIG. 12.
Figure 18:
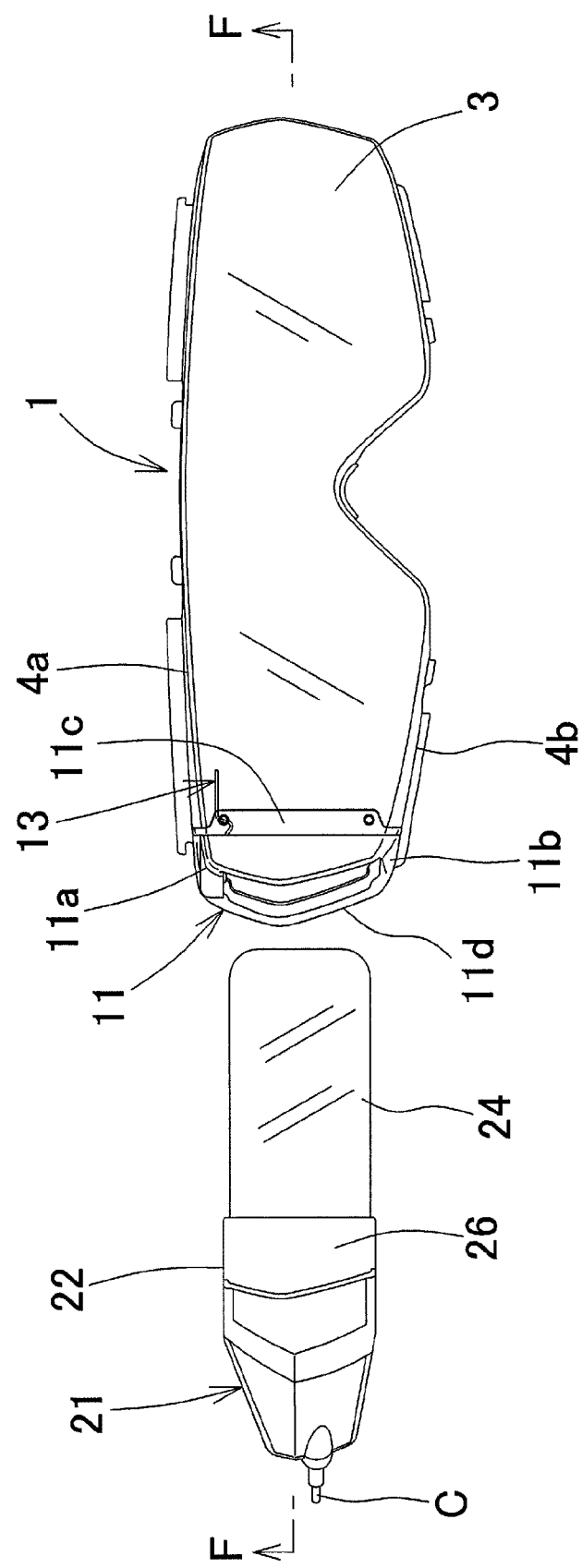
FIG. 18 is a front view of the main part of the face or head-mounted implement in a state illustrated in FIG. 17.
Figure 19:
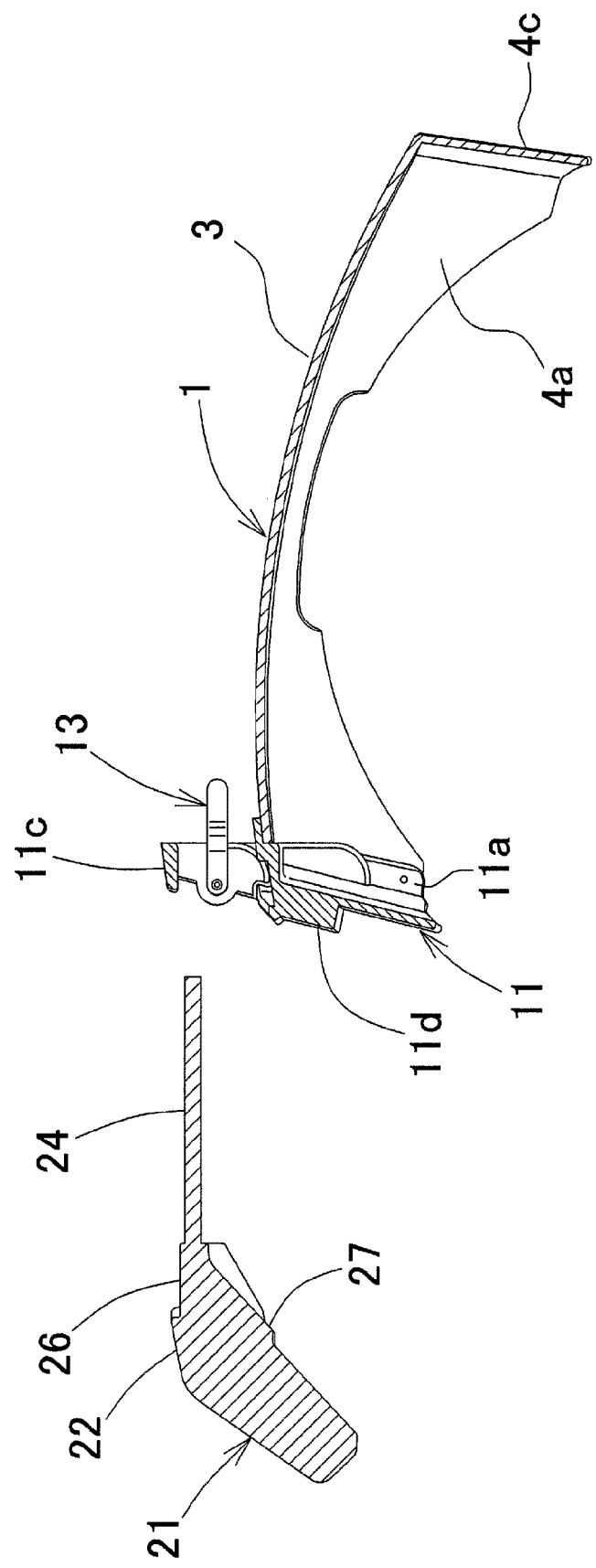
FIG. 19 is a sectional view taken along the line F-F in FIG. 18.

As illustrated in FIG. 11, the elastic pressing body 13 is a short flat plate shaped elastic metal plate or synthetic resin, or the like, and is fixed to the upper frame part 11a of the holding frame body 11 by a locking pin 15 protruded upward with respect to a base end, a leading end is used as an operation part 13a, and the projected engagement part 12 bent downward so as to have a substantially V-shape is formed in the width direction of an intermediate part.

Furthermore, although not illustrated, in a case in which the elastic pressing body 13 is fixed also to the lower frame part 11b of the holding frame body 11, or fixed only to the lower frame part 11b of the holding frame body 11, the locking pin 15 is protruded downward with respect to the base end, and the projected engagement part 12 is bent upward so as to have a substantially V-shape in the width direction of the intermediate part. The fixing of the elastic pressing body 13 is not limited to the locking pin 15, but may be screwing or bonding, or may be integrated molding in the case of synthetic resin. The projected engagement part 12 is merely an example, and is not limited to the part bent downward or upward so as to have the substantially V-shape as illustrated in the drawing.

In the illustration, in the wearable device 21, the display part 24 such as a liquid crystal plate that displays visual information such as characters and images projects from the body part 22 that incorporates an electronic circuit for information processing, and the like. A controller (not illustrated) for controlling the visual information as necessary is connected to the body part 22 through a cable C. The controller incorporates a power source such as a lithium rechargeable battery. However, such a power source may be incorporated in the body part 22 instead of the controller.

Furthermore, as illustrated in the drawing, the recessed engagement part 23 of the wearable device 21 is a groove formed in the substantially V-shape in the width direction of the upper surface 22a of the body part 22, and the projected engagement part 12 of the elastic pressing body 13 is configured such that engagement with this recessed engagement part 23 can be released by operating the operation part 13a at an end of this elastic pressing body 13 upward by a finger (operating the elastic pressing body 13 downward in a case in which the elastic pressing body 13 is provided in the lower frame part 11b of the holding frame body 11). In addition, the recessed engagement part 23 of the wearable device 21 is formed in a guide groove 25 formed in the length direction of the upper surface 22a of the body part 22, and when the body part 22 of the wearable device 21 is inserted into the holding frame body 11, the elastic pressing body 13 is guided along this guide groove 25, and the projected engagement part 12 of the elastic pressing body 13 is easily engaged with the recessed engagement part 23 of the wearable device 21. Although not illustrated, in a case in which the elastic pressing body 13 is provided in the lower frame part 11b of the holding frame body 11, the recessed engagement part 23 of the wearable device 21 is a groove formed in a substantially V-shape in the width direction of the lower surface 22b of the body part 22. The recessed engagement part 23 is merely an example, and is not limited to the groove formed in the substantially V-shape as illustrated in the drawings.

In the holding tool for a wearable device of the present invention described in the sixth embodiment, the upper frame part 11a, the lower frame part 11b, the front frame part 11c, and the rear frame part 11d of the holding frame body 11 are each formed in a substantially plate shape, a projected engagement part 14 is formed in at least one of the upper frame part 11a and the lower frame part 11b. In the illustration, the projected engagement part 14 is formed on the upper frame part 11a of the holding frame body 11. Furthermore, the flat plate shaped elastic pressing body 13 formed with the projected engagement part 12 detachably engaged with the projected engagement part 14 is provided in at least one of the upper surface 22a and the lower surface 22b of the body part 22 of the wearable device 21 from these upper surface 22a and the lower surface 22b toward the display part 24 of the wearable device 21. In the illustration, the elastic pressing body 13 is provided in the upper surface 22a of the body part 22.

Figure 39:
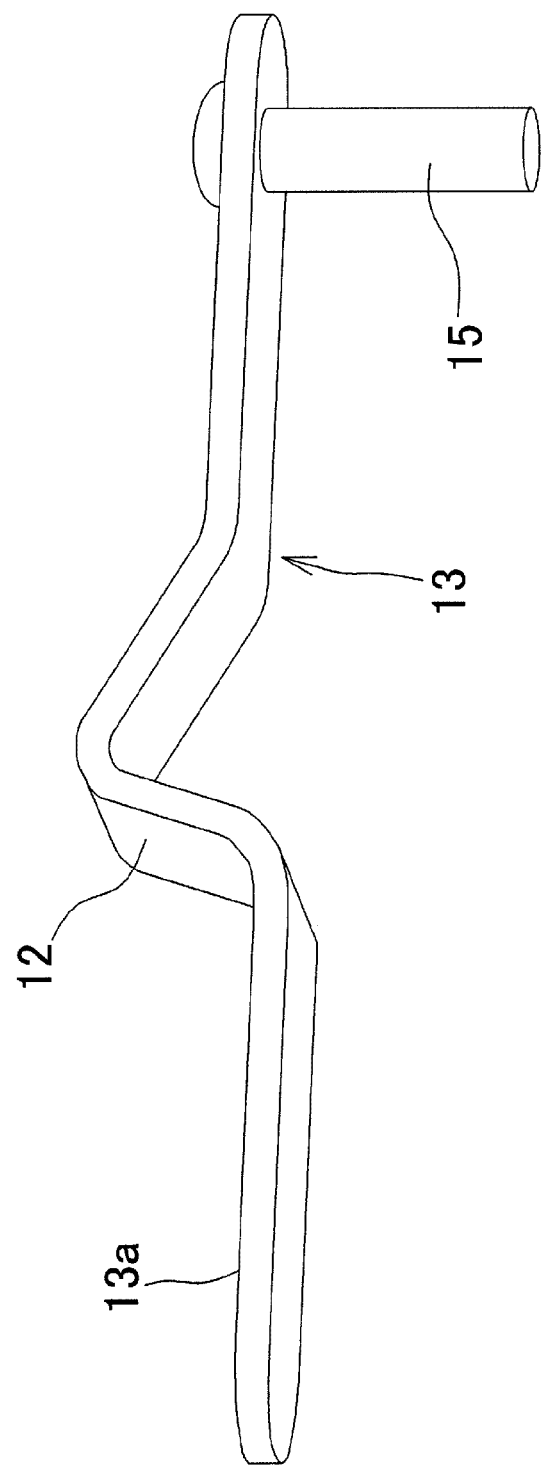
FIG. 39 is a perspective view of an elastic pressing body to be fixed to the wearable device illustrated in FIG. 37.

As illustrated in FIG. 39, the elastic pressing body 13 is a short flat plate shaped elastic metal plate or synthetic resin, or the like, and is fixed to the upper surface 22a of the body part 22 of the wearable device 21 by a locking pin 15 protruded downward with respect to a base end, a leading end is used as an operation part 13a, and a projected engagement part 12 bent upward so as to have a substantially V-shape is formed in the width direction of an intermediate part. Furthermore, although not illustrated, in a case in which the elastic pressing body 13 is fixed also to the lower surface 22b of the body part 22, or fixed only to the lower surface 22 of the body part 22, the locking pin 15 is protruded upward with respect to the base end, and the projected engagement part 12 is bent downward so as to have a substantially V-shape in the width direction of the intermediate part. The fixing of the elastic pressing body 13 is not limited to the locking pin 15, but may be screwing or bonding, or may be integrated molding in the case of synthetic resin. The projected engagement part 12 is merely an example, and is not limited to the part bent upward or downward so as to have the substantially V-shape as illustrated in the drawing.

As illustrated in the drawing, the projected engagement part 14 of the holding frame body 11 is a projection formed in the substantially V-shape in the width direction of an inner surface of the upper frame part 11a of the holding frame body 11, and the projected engagement part 12 of the elastic pressing body 13 is configured such that engagement with this projected engagement part 14 can be released by operating the operation part 13a at an end of this elastic pressing body 13 downward by a finger (operating the elastic pressing body 13 upward in a case in which the elastic pressing body 13 is provided in the lower surface 22b of the body part 22 of the wearable device 21). In addition, the projected engagement part 14 of the holding frame body 11 is formed in a guide groove 16 formed in the length direction of the inner surface of the upper frame part 11a, and when the body part 22 of the wearable device 21 is inserted into the holding frame body 11, the elastic pressing body 13 is guided along this guide groove 16, and the projected engagement part 12 of the elastic pressing body 13 slides over the projected engagement part 14 of the holding frame body 11, so that the projected engagement part 12 is easily engaged with the projected engagement part 14. Although not illustrated, in a case in which the elastic pressing body 13 is provided in the lower surface 22b of the body part 22 of the wearable device 21, the projected engagement part 14 of the holding frame body 11 is a projection formed in a substantially V-shape in the width direction of an inner surface of the lower frame part 11b of the holding frame body 11. The projected engagement part 14 is merely an example, and is not limited to the projection formed in the substantially V-shape as illustrated in the drawings.

Furthermore, in the holding tool of the present invention, in a state in which a part of a front end of the upper surface 22a of the body part 22 of the wearable device 21, or the like is in contact with the inner surface of the upper frame part 11a of the holding frame body 11, or a part of a front end of the lower surface 22b of the body part 22 of the wearable device 21, or the like is in contact with the inner surface of the lower frame part 11b of the holding frame body 11, the body part 22 of the wearable device 21 is inserted into the holding frame body 11. Consequently, the insertion state of the body part 22 of the wearable device 21 into the holding frame body 11 is stabilized.

In the holding tool of the present invention, in order to more reliably stabilize the insertion state of the body part 22 of the wearable device 21 into the holding frame body 11, as illustrated in FIGS. 9, 10 and FIGS. 37, 38, a recessed wall 26 may formed on a front surface 22c of the body part 22, a projected wall 27 may formed on a rear surface 22d of the body part 22, so that the recessed wall 26 may be in contact with an inner surface of the front frame part 11c of the holding frame body 11, and the projected wall 27 may be in contact with an inner end of the rear frame part 11d of the holding frame body 11.

In the face or head-mounted implement provided with the holding tool of the present invention, configured as described above, in a case of the glasses described in each of the first embodiment and the sixth embodiment, in a state in which the body part 22 of the wearable device 21 is inserted into the holding frame body 11 of the holding tool, the display part 24 of this wearable device 21 is disposed on the inner side of the lens 3 of the glasses, and in the case of the glasses described in each of the second embodiment and the third embodiment, in a state in which the body part 22 of the wearable device 21 is inserted into the holding frame body 11 of the holding tool, the display part 24 of this wearable device 21 is disposed on the outer side of the lens 3 of the glasses. Furthermore, in the case of the head band described in the fourth embodiment, or the helmet described in the fifth embodiment, in a state in which the body part 22 of the wearable device 21 is inserted into the holding frame body 11 of the holding tool, the display part 24 of this wearable device 21 is disposed in the region where a wearer can see the display part 24 of the wearable device 21.

Therefore, in the face or head-mounted implement provided with the holding tool of the present invention, in the case of the glasses described in the first embodiment or the sixth embodiment, there is not fear that in use outdoors at the time of rainfall or snowfall, use under bad environment such as inside of a factory where flying objects are flying, or dust is falling, the display part 24 of the wearable device 21 gets wet, is stained, or is damaged, the visual information on the display part 24 is difficult to be seen, and furthermore failure is caused.

Furthermore, in the holding tool of the present invention, when the wearable device 21 is detached, in the case of the glasses described in the first embodiment, in a state in which the glasses are slightly separated from a face while being worn, or is detached, or in each of the cases of the glasses described in the second embodiment, the glasses described in the third embodiment, the head band described in the fourth embodiment, or the helmet described in the fifth embodiment, in a state in which the glasses are worn, the operation part 13a of the elastic pressing body 13 is operated upward from the inside of the holding frame body 11 by a finger, and this elastic pressing body 13 is warped upward (although not illustrated, in a case in which the elastic pressing body 13 is provided in the lower frame part 11b of the holding frame body 11, the operation part 13a of the elastic pressing body 13 is operated downward, this elastic pressing body 13 is warped downward).

Then, the projected engagement part 12 of the elastic pressing body 13 is lifted, and the engagement between this projected engagement part 12 and the recessed engagement part 23 of the body part 22 of the wearable device 21 is released. In this state, when the body part 22 of the wearable device 21 is pulled out, the wearable device 21 is detached from the holding frame body 11 of the holding tool.

In the holding tool of the present invention, when the wearable device 21 is detached, in a case of the glasses described in the sixth embodiment, the glasses are slightly separated from a face while being worn, or is detached, the operation part 13a of the elastic pressing body 13 is operated downward from the inside of the holding frame body 11 by a finger, and this elastic pressing body 13 is warped downward (although not illustrated, in a case in which the elastic pressing body 13 is provided in the lower surface 22b of the body part 22 of the wearable device 21, the operation part of the elastic pressing body 13 is operated upward, this elastic pressing body 13 is warped upward).

Then, the projected engagement part 12 of the elastic pressing body 13 is pressed down, and the engagement between this projected engagement part 12 and the projected engagement part 14 of the upper frame part 11a of the holding frame body 11 is released. In this state, when the body part 22 of the wearable device 21 is pulled out, the wearable device 21 is detached from the holding frame body 11 of the holding tool.

Furthermore, in the holding tool of the present invention, in the embodiment described in each of the first to fifth embodiments, when the wearable device 21 is attached, a rear part of the body part 22 of the wearable device 21 is pinched by fingers, the display part 24 of the wearable device 21 is inserted from the holding frame body 11 of the holding tool, is disposed in a region where a wearer can see the display part on the inner side or the outer side of the lens 3 of the glasses, and a front part of the body part 22 is inserted into this holding frame body 11.

Then, the elastic pressing body 13 is guided along the guide groove 25 of the body part 22 of the wearable device 21, and the projected engagement part 12 of the elastic pressing body 13 is operated upward by an end of the upper surface 22a of the body part 22 (although not illustrated, in a case in which the elastic pressing body 13 is provided in the lower frame part 11b of the holding frame body 11, the elastic pressing body 13 is operated downward), and the projected engagement part 12 of this elastic pressing body 13 is engaged with the recessed engagement part 23 of the wearable device 21 so as to slide in the recessed engagement part 23, so that the wearable device 21 is attached to the holding frame body 11 of the holding tool.

In the holding tool of the present invention, also in the embodiment described in the sixth embodiment, when the wearable device 21 is attached, a rear part of the body part 22 of the wearable device 21 is pinched by fingers, the display part 24 of the wearable device 21 is inserted from the holding frame body 11 of the holding tool, is disposed on the inner side of the lens 3 of the glasses, and a front part of the body part 22 is inserted into this holding frame body 11.

Then, the elastic pressing body 13 is guided along the guide groove 16 of the inner surface of the upper frame part 11a of the holding frame body 11, and the projected engagement part 12 of the elastic pressing body 13 is pressed down by the projected engagement part 14 of the holding frame body 11 (although not illustrated, in a case in which the elastic pressing body 13 is provided in the lower surface 22b of the body part 22 of the wearable device 21, the elastic pressing body 13 is pressed up), slides over this projected engagement part 14, is engaged with this projected engagement part 14, so that the wearable device 21 is attached to the holding frame body 11 of the holding tool.

Therefore, in the face or head-mounted implement provided with the holding tool of the present invention, when the wearable device 21 is attached, positioning and reliable attachment can be performed by simple insertion operation, and when the device is detached, reliable detachment can be performed by simple operation of operating the elastic pressing body 13 upward or downward.

REFERENCE SIGNS LIST 1 lens body part
3 lens
8 clamping body
9 shell
9a cheek side part
11 holding frame body
11a upper frame part
11b lower frame part
11c front frame part
11d rear frame part
12 projected engagement part
13 elastic pressing body
13a operation part
14 projected engagement part
21 wearable device
22 body part
22a upper surface
22b lower surface
23 recessed engagement part
24 display part
26 recessed wall
27 projected wall

The invention claimed is:

1. A holding tool for a wearable device comprising:
a holding frame body wherein a body part of a wearable device is detachably attachable to said holding frame body,
a projected engagement part of an elastic pressing body provided in at least one of an upper frame part and a lower frame part of the holding frame body being detachably engaged with at least one of an upper surface and a lower surface of the body part of the wearable device,
wherein when the body part of the wearable device is inserted into the holding frame body, the projected engagement part of the elastic pressing body is engaged with the upper surface and/or the lower surface of the body part,
wherein engagement between the upper surface and/or the lower surface of the body part and the projected engagement part of the elastic pressing body is released by operating an operation part of the elastic pressing body upward and/or downward, to facilitate the wearable device being pulled out of the holding frame body.

2. The holding tool for a wearable device according to claim 1, wherein a recessed engagement part is formed in at least one of the upper surface and the lower surface of the body part of the wearable device, the projected engagement part of the elastic pressing body is operated upward and/or downward by an end of the upper surface and/or the lower surface of the body part, and the projected engagement part of the elastic pressing body is engaged with the recessed engagement part of the body part so as to slide in the recessed engagement part.

3. The holding tool for a wearable device according to claim 2, wherein the projected engagement part of the elastic pressing body is a part obtained by protruding an intermediate part of the elastic pressing body in a width direction so as to have a substantially V-shape, and the recessed engagement part of the body part of the wearable device is a groove formed in a substantially V-shape in a width direction of at least one of the upper surface and the lower surface of the body part.

4. The holding tool for a wearable device according to claim 1, wherein the holding frame body is a rectangular frame body including the upper frame part, the lower frame part, a front frame part, and a rear frame part.

5. The holding tool for a wearable device according to claim 1, wherein when a part of the upper surface of the body part of the wearable device is in contact with an inner surface of the upper frame part of the holding frame body, or a part of the lower surface of the body part of the wearable device is in contact with an inner surface of the lower frame part of the holding frame body, the body part of the wearable device is inserted into the holding frame body.

6. The holding tool for a wearable device according to claim 5, wherein a recessed wall is formed on a front surface of the body part of the wearable device, a projected wall is formed on a rear surface of the body part, the recessed wall is in contact with an inner surface of the front frame part of the holding frame body, and the projected wall is in contact with an inner end of the rear frame part of the holding frame body.

7. A face or head-mounted implement comprising:
the holding frame body of the holding tool according to claim 1, the holding frame body being provided in one side end of a lens body part, and wherein
a display part of the wearable device comprises glasses disposed on an inner side of a lens.

8. A face or head-mounted implement comprising:
the holding frame body of the holding tool according to claim 1, the holding frame body being provided in one side end of a lens body part, and wherein
a display part of the wearable device comprises glasses disposed on an outer side of a lens.

9. A face or head-mounted implement comprising:
the holding frame body of the holding tool according to claim 1, the holding frame body being provided in one side end of a clamping body formed in an inverted substantially U-shape and having elasticity, and wherein
a display part of the wearable device comprising a head band disposed in a region where a wearer is capable of seeing the display part.

10. A face or head-mounted implement comprising:
the holding frame body of the holding tool according to claim 1, the holding frame body being provided on an inner or outer side of a cheek side part on one side of a shell, and wherein
a display part of the wearable device comprises a helmet disposed in a region where a wearer is capable of seeing the display part.

11. A holding tool for a wearable device comprising:
a holding frame body wherein a body part of a wearable device is detachably attachable to said holding frame body,
a projected engagement part of an elastic pressing body provided in at least one of an upper surface and a lower surface the body part being detachably engaged with at least one of an upper frame part and a lower frame part of the holding frame body,
wherein when the body part of the wearable device is inserted into the holding frame body, the projected engagement part of the elastic pressing body is engaged with the upper frame part and/or the lower frame part of the holding frame body,
wherein engagement between the upper frame part and/or the lower frame part of the holding frame body and the projected engagement part of the elastic pressing body is released by operating an operation part of the elastic pressing body downward and/or upward, to facilitate the wearable device being pulled out of the holding frame body.

12. The holding tool for a wearable device according to claim 11, wherein a projected engagement part is formed in at least one of the upper frame part and the lower frame part of the holding frame body, and the projected engagement part of the elastic pressing body slides over the projected engagement part of the holding frame body to be engaged with the projected engagement part.

13. The holding tool for a wearable device according to claim 12, wherein the projected engagement part of the elastic pressing body is a part obtained by protruding an intermediate part of the elastic pressing body in a width direction so as to have a substantially V-shape, and the projected engagement part of the holding frame body is a projection formed in a substantially V-shape in a width direction of at least one of inner surfaces of the upper frame part and the lower frame part of the holding frame body.

14. The holding tool for a wearable device according to claim 11, wherein the holding frame body is a rectangular frame body including the upper frame part, the lower frame part, a front frame part, and a rear frame part.

15. The holding tool for a wearable device according to claim 11, wherein when a part of the upper surface of the body part of the wearable device is in contact with an inner surface of the upper frame part of the holding frame body, or a part of the lower surface of the body part of the wearable device is in contact with an inner surface of the lower frame part of the holding frame body, the body part of the wearable device is inserted into the holding frame body.

16. A face or head-mounted implement comprising:
the holding frame body of the holding tool according to claim 11, the holding frame body being provided in one side end of a lens body part, and wherein
a display part of the wearable device comprises glasses disposed on an inner side of a lens.

17. A face or head-mounted implement comprising:
the holding frame body of the holding tool according to claim 11, the holding frame body being provided in one side end of a lens body part, and wherein
a display part of the wearable device comprises glasses disposed on an outer side of a lens.

18. A face or head-mounted implement comprising:
the holding frame body of the holding tool according to claim 11, the holding frame body being provided in one side end of a clamping body formed in an inverted substantially U-shape and having elasticity, and wherein
a display part of the wearable device comprising a head band disposed in a region where a wearer is capable of seeing the display part.

19. A face or head-mounted implement comprising:
the holding frame body of the holding tool according to claim 11, the holding frame body being provided on an inner or outer side of a cheek side part on one side of a shell, and wherein
a display part of the wearable device comprises a helmet disposed in a region where a wearer is capable of seeing the display part.

* * * * *